US008865078B2

(12) United States Patent
Chiou et al.

(10) Patent No.: US 8,865,078 B2
(45) Date of Patent: Oct. 21, 2014

(54) APPARATUS FOR SINGLE-MOLECULE DETECTION

(75) Inventors: Chung-Fan Chiou, Hsinchu (TW);
Rung-Ywan Tsai, Taoyuan (TW);
Yu-Tang Li, Tucheng (TW);
Chih-Tsung Shih, Hsinchu (TW);
Ming-Chia Li, Dajia Township,
Taichung County (TW); Chang-Sheng Chu, Hsinchu (TW); Shuang-Chao Chung, Zhongli (TW); Jung-Po Chen,
Toufen Township, Miaoli County (TW);
Ying-Chih Pu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/805,411

(22) Filed: Jul. 29, 2010

(65) Prior Publication Data
US 2011/0306143 A1    Dec. 15, 2011

Related U.S. Application Data

(63) Continuation-in-part of application No. 12/801,503, filed on Jun. 11, 2010.

(51) Int. Cl.
| | |
|---|---|
| G01N 21/00 | (2006.01) |
| G01N 21/01 | (2006.01) |
| G01N 21/64 | (2006.01) |
| G01N 33/50 | (2006.01) |
| G01N 33/52 | (2006.01) |
| G01N 33/487 | (2006.01) |
| C40B 60/12 | (2006.01) |
| B82Y 15/00 | (2011.01) |
| G01N 21/77 | (2006.01) |

(52) U.S. Cl.
CPC ............ *B82Y 15/00* (2013.01); *G01N 21/7703* (2013.01); *G01N 21/648* (2013.01); *Y10S 977/954* (2013.01); *Y10S 977/957* (2013.01); *Y10S 977/958* (2013.01)

USPC .................. 422/82.11; 422/82.05; 422/82.08; 385/10; 385/12; 385/131; 385/144; 435/287.2; 435/288.4; 435/288.7; 435/6.1; 435/6.12; 436/94; 436/96; 436/172; 356/73.1; 977/954; 977/957; 977/958

(58) Field of Classification Search
None
See application file for complete search history.

(56) References Cited

U.S. PATENT DOCUMENTS 4,748,111 A    5/1988   Dattagupta et al.
4,790,614 A  * 12/1988  Imoto et al. ................... 385/130
(Continued)

FOREIGN PATENT DOCUMENTS

CN         1545619 A      11/2004
CN         1576844 A       2/2005
(Continued)

OTHER PUBLICATIONS

E. Metwalli et al., Surface characterization of mono-, di-, and tri-aminosilane treated glass substrates, 2006, J. of Colloid and Interface Science 298: 825-831.*

(Continued)

*Primary Examiner* — Jill Warden
*Assistant Examiner* — Timothy G Kingan
(74) *Attorney, Agent, or Firm* — Finnegan, Henderson, Farabow, Garrett & Dunner, LLP

(57) ABSTRACT

An apparatus for detecting an object capable of emitting light. The apparatus includes a light source and a waveguide. The waveguide includes a core layer and a first cladding layer. At least one nanowell is formed in at least the first cladding layer. The apparatus further includes a light detector. The light detector can detect a light emitted from a single molecule object contained in the at least one nanowell.

52 Claims, 18 Drawing Sheets

(56) References Cited

U.S. PATENT DOCUMENTS

| | | | |
|---|---|---|---|
| 5,034,613 A | 7/1991 | Denk et al. | |
| 5,162,887 A | 11/1992 | Dierschke | |
| 5,185,832 A * | 2/1993 | Coutandin et al. | 385/43 |
| 5,405,747 A | 4/1995 | Jett et al. | |
| 5,460,975 A * | 10/1995 | Freitag et al. | 436/500 |
| 5,674,743 A | 10/1997 | Ulmer | |
| 5,717,602 A | 2/1998 | Kenning | |
| 5,750,341 A | 5/1998 | Macevicz | |
| 5,965,875 A | 10/1999 | Merrill | |
| 6,013,434 A | 1/2000 | Tregear et al. | |
| 6,091,874 A * | 7/2000 | Higashi et al. | 385/130 |
| 6,123,819 A | 9/2000 | Peeters | |
| 6,153,737 A | 11/2000 | Manoharan et al. | |
| 6,197,513 B1 | 3/2001 | Coull et al. | |
| 6,210,973 B1 | 4/2001 | Pettit | |
| 6,255,083 B1 | 7/2001 | Williams | |
| 6,344,653 B1 | 2/2002 | Webb et al. | |
| 6,374,019 B1 * | 4/2002 | Gustavsson | 385/42 |
| 6,762,048 B2 | 7/2004 | Williams | |
| 6,917,726 B2 * | 7/2005 | Levene et al. | 385/12 |
| 6,946,249 B2 | 9/2005 | Head et al. | |
| 7,013,054 B2 | 3/2006 | Levene et al. | |
| 7,015,485 B2 | 3/2006 | Kitagawa | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,060,440 B1 | 6/2006 | Kless | |
| 7,167,735 B2 | 1/2007 | Uchida et al. | |
| 7,170,050 B2 | 1/2007 | Turner et al. | |
| 7,181,122 B1 | 2/2007 | Levene et al. | |
| 7,226,777 B2 | 6/2007 | Kawamura et al. | |
| 7,229,799 B2 | 6/2007 | Williams | |
| 7,282,337 B1 | 10/2007 | Harris | |
| 7,292,742 B2 | 11/2007 | Levene et al. | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,316,930 B1 | 1/2008 | Montalbo | |
| 7,329,492 B2 | 2/2008 | Hardin et al. | |
| 7,361,466 B2 | 4/2008 | Korlach et al. | |
| 7,384,797 B1 * | 6/2008 | Blair | 436/524 |
| 7,416,844 B2 | 8/2008 | Korlach et al. | |
| 7,485,424 B2 | 2/2009 | Korlach et al. | |
| 7,486,865 B2 | 2/2009 | Foquet et al. | |
| 7,767,441 B2 | 8/2010 | Chiou et al. | |
| 7,805,081 B2 | 9/2010 | Lundquist et al. | |
| 7,943,305 B2 | 5/2011 | Korlach et al. | |
| 7,943,307 B2 | 5/2011 | Korlach et al. | |
| 2002/0090630 A1 | 7/2002 | Hazama | |
| 2002/0110839 A1 * | 8/2002 | Bach et al. | 435/7.9 |
| 2002/0154315 A1 | 10/2002 | Myrick | |
| 2003/0087242 A1 | 5/2003 | Mirkin et al. | |
| 2003/0092005 A1 | 5/2003 | Levene et al. | |
| 2003/0143724 A1 | 7/2003 | Cerrina et al. | |
| 2004/0038331 A1 | 2/2004 | Reddy et al. | |
| 2005/0089298 A1 * | 4/2005 | Maxwell et al. | 385/144 |
| 2005/0100919 A1 | 5/2005 | Stanton et al. | |
| 2005/0201899 A1 | 9/2005 | Weisbuch | |
| 2005/0208557 A1 | 9/2005 | Korlach et al. | |
| 2005/0275839 A1 | 12/2005 | Robinson et al. | |
| 2006/0057606 A1 | 3/2006 | Korlach et al. | |
| 2006/0068506 A1 | 3/2006 | Uyeda et al. | |
| 2006/0134666 A1 | 6/2006 | Korlach et al. | |
| 2006/0160113 A1 | 7/2006 | Korlach et al. | |
| 2006/0228722 A1 * | 10/2006 | Kim et al. | 435/6 |
| 2007/0026447 A1 | 2/2007 | Korlach et al. | |
| 2007/0036511 A1 | 2/2007 | Lundquist et al. | |
| 2007/0083122 A1 | 4/2007 | Alfano et al. | |
| 2007/0141598 A1 | 6/2007 | Turner et al. | |
| 2008/0037008 A1 | 2/2008 | Shepard et al. | |
| 2008/0050747 A1 * | 2/2008 | Korlach et al. | 435/6 |
| 2008/0061683 A1 * | 3/2008 | Bertram | 313/504 |
| 2008/0081769 A1 | 4/2008 | Hassibi | |
| 2008/0087843 A1 | 4/2008 | Medintz et al. | |
| 2008/0176769 A1 * | 7/2008 | Rank et al. | 506/32 |
| 2008/0177139 A1 * | 7/2008 | Courtney et al. | 600/109 |
| 2008/0199932 A1 | 8/2008 | Hanzel et al. | |
| 2008/0227654 A1 | 9/2008 | Korlach et al. | |
| 2008/0241833 A1 | 10/2008 | Williams | |
| 2009/0015831 A1 | 1/2009 | Yguerabide et al. | |
| 2009/0082212 A1 | 3/2009 | Williams | |
| 2009/0087850 A1 | 4/2009 | Eid et al. | |
| 2009/0137007 A1 | 5/2009 | Korlach et al. | |
| 2009/0146076 A1 | 6/2009 | Chiou et al. | |
| 2009/0170074 A1 | 7/2009 | Williams | |
| 2010/0009872 A1 | 1/2010 | Eid et al. | |
| 2010/0035268 A1 | 2/2010 | Beecham et al. | |
| 2010/0055666 A1 * | 3/2010 | Wimberger-Friedl et al. | 435/4 |
| 2010/0065726 A1 * | 3/2010 | Zhong et al. | 250/227.24 |
| 2010/0075328 A1 | 3/2010 | Bjornson et al. | |
| 2010/0093068 A1 | 4/2010 | Williams | |
| 2010/0255463 A1 | 10/2010 | Harsin et al. | |
| 2010/0255487 A1 | 10/2010 | Beecham et al. | |
| 2010/0256016 A1 | 10/2010 | Blair et al. | |
| 2010/0256918 A1 | 10/2010 | Chen et al. | |
| 2010/0304358 A1 | 12/2010 | Nie et al. | |
| 2011/0014612 A1 | 1/2011 | Hendricks et al. | |
| 2011/0111401 A1 | 5/2011 | Korlach et al. | |
| 2011/0210094 A1 * | 9/2011 | Gray et al. | 216/12 |
| 2011/0300534 A1 | 12/2011 | Chiou et al. | |

FOREIGN PATENT DOCUMENTS

| | | |
|---|---|---|
| CN | 101654712 A | 2/2010 |
| EP | 1309719 | 2/2002 |
| JP | 62-165129 | 7/1987 |
| JP | 04-303972 | 10/1992 |
| JP | 4-303972 | 10/1992 |
| JP | 05-118991 | 5/1993 |
| JP | 2001-161696 | 6/2001 |
| JP | 2003-502847 | 1/2003 |
| JP | 2003-295064 | 10/2003 |
| JP | 2003-532123 A | 11/2003 |
| JP | 2004-219330 | 8/2004 |
| JP | 2005-127795 A | 5/2005 |
| JP | 2005172840 | 6/2005 |
| JP | 2006-220645 A | 8/2006 |
| JP | 2008-520975 | 6/2008 |
| JP | 2009-537148 A | 10/2009 |
| WO | WO 01/42768 | 6/2001 |
| WO | WO 00/70073 A9 | 4/2002 |
| WO | WO 02/066683 | 8/2002 |
| WO | WO 02/073158 | 9/2002 |
| WO | WO-03/003015 | 1/2003 |
| WO | WO 2005/019419 A2 | 3/2005 |
| WO | WO 2006/073504 A2 | 7/2006 |
| WO | WO 2007/091280 A1 | 8/2007 |
| WO | WO 2007/119067 | 10/2007 |
| WO | WO 2008/002101 | 1/2008 |
| WO | WO 2008/032096 | 3/2008 |
| WO | WO 2008/032096 A2 | 3/2008 |
| WO | WO 2009/017678 | 2/2009 |
| WO | WO 2009/056065 A1 | 5/2009 |
| WO | WO 2009/145818 | 12/2009 |

OTHER PUBLICATIONS

T. D. Harris et al., "Single-Molecule DNA Sequencing of a Viral Genome," Science, vol. 320, pp. 106-109 (2008).

J. D. Levin, "Position-dependent effects of locked nucleic acid (LNA) on DNA sequencing and PCR primers," Nucleic Acids Research, vol. 34, No. 20, e142 (2006).

A. L. McGuire et al., "The future of personal genomics," Science, vol. 317, p. 1687 (2007).

I. L. Medintz et al., "Quantum dot bioconjugates for imaging, labelling and sensing," Nature Materials, vo. 4, pp. 435-446 (2005).

W. E. Moerner et al., "Review Article: Methods of single-molecule fluorescence spectroscopy and microscopy," Review of Scientific Instruments, vol. 74, No. 8, pp. 3597-3619 (2003).

M. Schena, "Microarray Biochip Technologies," p. 28 and pp. 76-78 (2000).

(56) References Cited

OTHER PUBLICATIONS

J. Shendure et al., "Advanced sequencing technologies: methods and goals," Nat. Rev. Genet., vol. 5, pp. 335-344 (2004).
J. Shendure et al., "Accurate multiplex polony sequencing of an evolved bacterial genome," Science, vol. 309, pp. 1728-1732 (2005).
D. C. Tessier et al., "Ligation of single-stranded oligodeoxyribonucleotides by T4 RNA ligase," Anal. Biochem., vol. 158, pp. 171-178 (1986).
N. G. Walter, et al., "Do-it-yourself guide: how to use the modern single-molecule toolkit," Nature Methods, vol. 5, pp. 475-489 (2008).
C. Y. Zhang et al., "Single-quantum-dot-based DNA nanosensor," Nature Materials, vol. 4, pp. 826-831 (2005).
Examiner's First Report issued by the Australian Patent Office, dated Jun. 20, 2011, in an Australian patent application No. 2010249264 (2 pages).
Spring et al., "Introduction to fluorescence microscopy," Nikon microscopy, 10 pages.
International Search Report and Written Opinion, issued by International Searching Authority, dated Jul. 7, 2011, in International application No. PCT/CN2011/071814 (14 pages).
Extended European search report, issued by the European Patent office, dated Aug. 12, 2011, in European patent application No. 10750363.3 (17 pages).
Extended European search report, issued by the European Patent office, dated Aug. 16, 2011, in European patent application No. 10196884.0 (10 pages).
Anker et al., "Magnetically-modulated Optical Nanoprobes (MagMOONs) and Systems," Journal of Magnetism and Magnetic Materials 293:655-662 (2005).
Cao, Y.M. et al., "DNA-modified core-shell Ag/Au nanoparticles," J. Am. Chem. Soc., vol. 123, pp. 7961-7962 (2001).
Cheng "High-Speed DNA-Sequence Analysis" Prog. Biochem. Biophys. 22:223-227 (1995) (English abstract on p. 227).
Dapprich et al. "DNA Attachment to Optically Trapped Beads in Microstructures Monitored by Bead Displacement" Bioimaging 6:25-32 (1998).
Han et al., "High performance electrophoresis system for site-specific entrapment of nanoparticles in a nanoarray," Proc. of SPIE 7574:75740L (2010).
Kang et al., "Synthesis and Characterization of Nanometer-Size $Fe_3O_4$ and $\gamma$-$Fe_2O_3$ Particles," Chem. Mater. 8(9):2209-2211 (1996).
McNaughton et al., "Fabrication of uniform half-shell magnetic nanoparticles and microspheres with applications as magnetically modulated optical nanoprobes," Submitted to Applied Physics Letters, Jun. 16, 2005; 6 pp. [online]; retrieved from the Internet: http://arxiv.org/abs/cond-mat/0506418.
Metzker "Sequencing technologies—the next generation," Nature Reviews Genetics 11:31-46 (2010).
Nandwana et al., "Size and Shape Control of Monodisperse FePt Nanoparticles," J. Phys. Chem. C 111(11):4185-4189 (2007).
Ozsolak et al., "Direct RNA sequencing," Nature 461:814-818 (2009).
Park et al., "Multifunctional Nanoparticles for Photothermally Controlled Drug Delivery and Magnetic Resonance Imaging Enhancement," Small 4(2):192-196 (2008).
Perro et al., "Design and synthesis of Janus micro- and nanoparticles," J. Mater. Chem. 15:3745-3760 (2005).
Qiu et al., "Fluorescence single-molecule counting assays for high-sensitivity detection of cytokines and chemikines," Clin. Chem. 53(11):2010-2012 (2007).
Ramadan et al., "Customized trapping of magnetic particles," Microfluidics and Nanofluidics 6(1):53-62 (2009).
Schmitt et al., "High-Refractive-Index Waveguide Platforms for chemical and biosensing," in Optical Guided-Wave Chemical and Biosensors I. M. Zourob and A. Lakhtakia (Eds.), 2010; pp. 7 and 21.
Velev et al., "Particle-localized AC and DC manipulation and electrokinetics," Ann. Rep. Prog. Chem., Sect. C 105:213-246 (2009).
Wang et al., "One-Pot Synthesis and Bioapplication of Amine-Functionalized Magnetite Nanoparticles and Hollow Nanospheres," Chem. Eur. J. 12:6341-6347 (2006).
Wu et al., "Bioinspired Nanocorals with Decoupled Cellular Targeting and sensing Functionality," Small 6(4):503-507 (Feb. 22, 2010).
Zheng et al., "Quasicubic $\alpha$-$Fe_2O_3$ Nanoparticles with Excellent Catalytic Performance," J. Phys. Chem. B 110(7) (2006).
Office Action (Patent Examination Report No. 1) dated Oct. 15, 2012, issued in Australian Patent Application No. 2011229691.
Examiner's Report dated Apr. 5, 2013, issued in Canadian Patent Application No. 2,763,100.
English translation of Office Action (Notice to Submit a Response) dated Apr. 2, 2013, issued in Korean Patent Application No. 10-2011-7031724 (4 pages).
English translation of Notification of Reason(s) for Refusal, issued by Japanese Patent Office, mailed Jul. 2, 2013, in Japanese Patent App. No. 2011-288867 (4 pages).
Adessi et al., "Solid phase DNA amplification: characterization of primer attachment and amplification mechanisms," Nucleic Acids Research, vol. 28, No. 20, e87 (2000).
Blackard et al., "Intrahepatic cytokine expression is downregulated during HCV/HIV co-infection," Journal of Medical Virology, vol. 78, pp. 202-207 (2006).
Eid et al., "Real-time DNA sequencing from single polymerase molecules," Science, vol. 323, pp. 133-138 (2009).
Fife et al., "Multi-aperture image sensor with 0.7 μm pixels in 0.11 μm CMOS technology," IEEE Journal of Solid-State Circuits, vol. 43, No. 12, pp. 2990-3005 (2008).
Kamtekar et al., "Insights into strand displacement and processivity from the crystal structure of the protein-primed DNA polymerase of bacteriophage φ29," Mol Cell, 16: 609-618 (2004).
Kim et al., "Crystal structure of *Thermus aquaticus* DNA polymerase," Nature, 376: 612-616 (1995).
Korlach et al., "Selective aluminum passivation for targeted immobilization of single DNA polymerase molecules in zero-mode waveguide nanostructures," PNAS, vol. 105, No. 4, pp. 1176-1181 (2008).
Levene et al., "Zero-mode waveguides for single-molecule analysis at high concentrations," Science, vol. 299, pp. 682-686 (2003).
Neamen, Semiconductor Physics and Devices, pp. 17-19, McGraw-Hill (2d ed. 1997).
Niclass et al., "A single photon avalanche diode array fabricated in deep-submicron CMOS technology," Proceedings of the conference on Design, automation and test in Europe: Proceedings, Munich, Germany, pp. 81-86 (2006).
Spring et al., "Introduction to fluorescence microscopy," Nikon microscopy, 10 pages, 2010.
Stevens et al., "Low-crosstalk and low-dark-current CMOS image-sensor technology using a hole-based detector," Digest of Technical Papers of 2008 IEEE International Solid-State circuits Conference, pp. 60-61 and pp. 595 (2008).
Sze, Physics of Semiconductor Devices, pp. 674-675, John Wiley & Sons, Inc. (3d ed. 2007).
Wang et al., "Single-molecule tracing on a fluidic microchip for quantitative detection of low-abundance nucleic acids," JACS, vol. 127, pp. 5354-5359 (2005).
Notification of Transmittal of the International Search Report and the Written Opinion of the International Search Authority, or the Declaration, issued by International Search Authority, on Jun. 17, 2010, in PCT Application No. PCT/CN2010/070973.
English translation of Notice of Reasons for Rejection issued by Japanese Patent Office, mailed Dec. 3, 2013, in Japanese Patent Application No. JP2013-501618 (4 pages).
Japanese Office Action for application No. 2011-553266, dated Mar. 3, 2014, 8 pgs.

* cited by examiner

APPARATUS FOR SINGLE-MOLECULE DETECTION

This application is a continuation-in-part application of application Ser. No. 12/801,503 filed Jun. 11, 2010, the entire content of which is incorporated herein by reference.

TECHNICAL FIELD

The present disclosure relates to a detection apparatus, and the method of using the apparatus to detect an object. Further, the present disclosure relates to a detection apparatus that is able to detect a light of low intensity emitted from an object, such as a single molecule object.

BACKGROUND

The Human Genome Project (HGP) spurred a great increase in sequencing throughput and this, along with technical improvements, resulted in a corresponding drop in sequencing costs. In contrast to the 13 years and cost of nearly three billion US dollars, per genome sequencing costs have been reduced significantly—indeed two individual genomes have recently been completed (McGuire et al., *Science* 317: 1687 (2007)). Personal genomes represent a paradigm shift in medical treatment for both patients and health care providers. By managing genetic risk factors for disease, health care providers can more readily practice preventative medicine and provide customized treatment. With large banks of completed genomes, drug design and administration can be more efficient, pushing forward the nascent field of pharmacogenomics.

Most conventional chemical or biochemical assays are based on "bulk" measurements. In such measurements, a collective behavior of a plurality of molecules within a certain volume of a sample solution is measured to determine the properties of the molecules. Recently, the detection of single molecule became possible. Single-molecule detection provides another option for chemical and biochemical assays, which offers much higher sensitivity and provides more detailed information than conventional bulk measurements, and soon became a new trend. An overview of the criteria for achieving single-molecule detection is discussed in, for example, the review articles by Moerner et al. (Moerner and Fromm, "REVIEW ARTICLE: Methods of single-molecule fluorescence spectroscopy and microscopy", Review of Scientific Instruments 74(8): 3597-3619 (2003)) and Walter et al. (Walter, et al., "Do-it-yourself guide: how to use the modern single-molecule toolkit", Nature Methods 5: 475-489 (2008)). These articles also discuss methods and apparatus that have been used or proposed for single-molecule detection.

U.S. Pat. No. 7,170,050 provides a zero-mode waveguide (ZMW) for single-molecule detection. The ZMW consists of a metal film and a plurality of holes formed therein, which constitute the core regions of the ZMW. In a ZMW, propagation of light having a wavelength longer than a cutoff wavelength in a core region is prohibited. When a light having a wavelength longer than the cutoff wavelength is incident to the entrance of the waveguide, the light will not propagate along the longitudinal direction of the core region. Instead, the light intensity will decay exponentially along the longitudinal direction of the core region, forming an evanescent field at the entrance of the waveguide. This offers a specific excitation zone, within which molecule is excited and the emitted fluorescent light is captured by confocal microscope. However, the detectable number of ZMWs is limited by the numerical aperture (NA) of the confocal microscope and the throughput is limited. U.S. Pat. No. 7,486,865 provides a recessed ZMW formed by extending the ZMW into the underlying substrate. This configuration allows a more tunable observation volume and higher signal level for optics placed below the waveguide. However, this configuration still has scale-up issue and limited throughput problems.

Therefore, there is a need for an apparatus to detect an object, especially an object emitting light of low intensity such as a single-molecule object.

SUMMARY

In accordance with the present disclosure, there is provided an apparatus for detecting an object capable of emitting light. The apparatus comprises a waveguide. The waveguide comprises a core layer and a first cladding layer. At least one nanowell is formed in at least the first cladding layer. The apparatus further comprises a light detector. The light detector can detect a light emitted from a single molecule object contained in the at least one nanowell.

Also in accordance with the present disclosure, there is provided a method of detecting a single molecule, comprising the steps of: (a) emitting, by a light source, an incident light; (b) coupling, by a coupler, the incident light into a waveguide, forming an excitation light in the waveguide; (c) forming, by the excitation light and at least one nanowell formed in at least a cladding layer of the waveguide, an effective excitation zone; and (d) exciting, by the excitation light, a single molecule object in the effective excitation zone, to cause the single molecule object to emit a light to be detected by a detector.

Also in accordance with the present disclosure, there is provided a method of sequencing a nucleic acid, comprising the steps of (a) providing a detection apparatus comprising: a waveguide comprising: a core layer; and a first cladding layer; at least one nanowell formed in at least the first cladding layer; and a detector; (b) providing at least one nucleic acid molecule; (c) locating the at least one nucleic acid molecule individually within the at least one nanowell; (d) performing single molecule sequencing-by-synthesis of the at least one nucleic acid molecule, wherein the single molecule nucleic acid sequencing-by-synthesis leads to emission of light correlated to the identity of at least one base in the nucleic acid; (e) detecting the light with the detector, resulting in an output signal; and (f) processing the output signal to determine an identity of at least one base in the nucleic acid.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory and are not restrictive of the present disclosure, as claimed.

The accompanying drawings, which are incorporated in and constitute a part of this specification, illustrate one (several) embodiment(s) of the present disclosure and together with the description, serve to explain the principles of the present disclosure.

DETAILED DESCRIPTION

Figure 1:
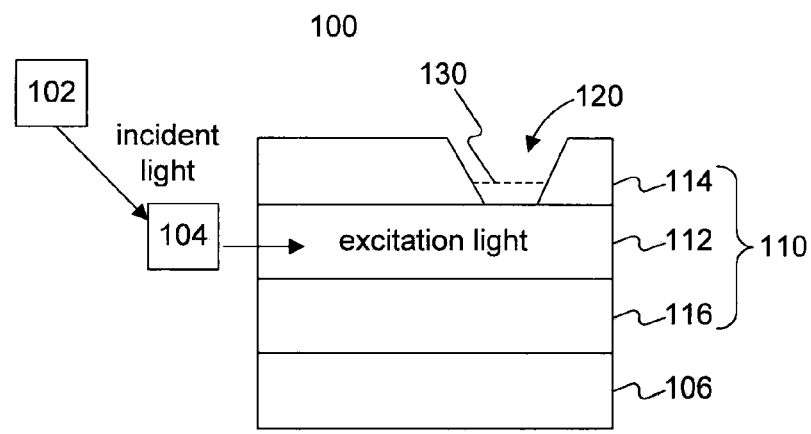
FIG. 1 is a schematic view of a detection apparatus consistent with the present disclosure.

The apparatuses for conventional bulk assay, including miniaturized bulk assay, and apparatuses for single-molecule detection may share many essential elements and may have similar apparatus structures. However, to realize single-molecule detection, a system may need to fulfill at least the following two criteria: 1) it should have both a confined excitation space and a confined observation space, and 2) the above-noted two spaces should fully or partially overlap and the overlapping region should be small enough to ensure that the light emitted from the target single molecule is higher than the background to provide a detectable signal-to-noise ratio (SNR). For example, the volume of the overlapping region should be on the order of or smaller than femto-liter level. More particularly, the volume of the overlapping region should be in the range from atto-liter to zepto-liter. Moreover, it may also be important to prevent the excitation light from reaching the detector.

Embodiments consistent with the present disclosure include a detection apparatus and method of using the detection apparatus for detecting an object, such as a single molecule object. The detection apparatus is capable of detecting weak light emitted from the object.

Hereinafter, embodiments consistent with the present disclosure will be described in detail with reference to drawings. Wherever possible, the same reference numbers will be used throughout the drawings to refer to the same or like parts.

1. APPARATUS OF THE PRESENT DISCLOSURE

In one aspect, the disclosure relates to a detection apparatus which is capable of detecting an object, such as a single-molecule object. Consistent with the present disclosure, the object may be a source of luminescence, such as a fluorescent dye molecule, a phosphorescent dye molecule, a quantum dot, or a light-emitting nanoparticle. The object may also be a light-scattering particle. In addition, the object may be a target molecule without light emitting capability, but may be attached to a labeling object which is capable of emitting light (e.g., a fluorescent dye molecule, a phosphorescent dye molecule, or a quantum dot). A certain labeling object may be capable of being attached to a specific target molecule. Thus, the target molecule may be identified via the labeling object. More than one labeling object may be attached to one target molecule.

1.1 Overview of the Apparatus

The detection apparatus consistent with the present disclosure may comprise at least one light source, which can emit a light, which may then be at least partially coupled into the waveguide as an excitation light to excite the object. The light source may be, for example, laser such as He—Ne laser and laser diode (LD), light emitting diode (LED), organic light emitting diode (OLED), quantum dot light emitting diode (OLED), fiber light, or arc discharge fluorescent lamp.

The detection apparatus consistent with the present disclosure may comprise a waveguide. The waveguide may be a channel waveguide or a planar waveguide. The waveguide may comprise a core layer and at least one cladding layer. For example, if the waveguide is a channel waveguide, it may comprise a core layer and a cladding layer surrounding the core layer. As another example, if the waveguide is a planar waveguide, it may comprise a core layer and one cladding layer arranged on the core layer or two cladding layers sandwiching the core layer. The core layer has a larger refractive index than the at least one cladding layer. The excitation light may propagate in the core layer of the waveguide.

Consistent with the present disclosure, at least one nanowell may be formed in at least the at least one cladding layer. The nanowell may comprise an upper opening and a bottom surface, wherein the upper opening may be larger than the bottom surface. The nanowell may extend through partial thickness of the at least one cladding layer, full thickness of the at least one cladding layer, full thickness of the at least one cladding layer and partial thickness of the core layer, or the full thickness of the at least one cladding layer and full thickness of the core layer. An effective excitation zone may be formed near the bottom of the nanowell. The lower boundary of the effective excitation zone may be the bottom of the nanowell. The upper boundary of the effective excitation zone may be defined by the distance to which the excitation light can reach in the nanowell in the direction perpendicular to the longitudinal direction of the core layer (hereinafter, vertical direction).

The detection apparatus consistent with the present disclosure may comprise a plurality of nanowells. Therefore, the apparatus may also be used to monitor a large number of objects.

The detection apparatus consistent with the present disclosure may comprise a light detector detecting light emitted from the object. Consistent with the present disclosure, the light detector may comprise an optical sensor, which is capable of at least partially absorbing light incident thereon and generating output signals in response to the light. The optical sensor may be, e.g., a p-n photodiode, a p-i-n photodiode, a multi-junction photodiode, an avalanche photodiode (APD), a phototransistor, a quantum-well infrared photodetector (QWIP), a photoconductive type optical sensor, a photovoltaic type optical sensor, a thin-film on ASIC (TFA), a metal-semiconductor-metal (MSM) photodetector, a charge coupled device (CCD), a CMOS sensor, or a combination thereof.

Consistent with the present disclosure, the light detector may comprise a control circuit for controlling the operation of the light detector. The control circuit may comprise a circuit of signal amplifier, A/D convertor, integrator, comparator, logic circuit, readout circuit, memory, microprocessor, clock, and/or address.

Consistent with the present disclosure, the light detector may be arranged at a place that the light emitted from the object can reach. For example, the light detector may be arranged at the opposite side of the core layer with respect to the nanowell. That is, if the nanowell is arranged on one side of the core layer in the vertical direction, the light detector may then be arranged on the other side of the core layer in the vertical direction.

The detection apparatus consistent with the present disclosure may comprise a light coupler. The light coupler may couple at least part of the light emitted from the at least one light source into the waveguide. The light coupler may be, e.g., a prism coupler, a grating coupler, a side-injection coupler, a vertical-injection coupler, or a co-directional coupler.

1.2 Exemplary Apparatuses

Referring to FIG. 1, a schematic view of a detection apparatus 100 consistent with the present disclosure is illustrated. In some embodiments, the detection apparatus 100 may comprise a light source 102, a light coupler 104, a light detector 106, and a planar waveguide 110. The planar waveguide 110 may be formed on a substrate (not shown). The light detector 106 may be formed on or in the substrate.

The light source 102 may emit a light, which may be at least partially coupled into the planar waveguide 110 by the light coupler 104. Light coupled into the planar waveguide 110 may propagate in the core layer of the planar waveguide 110 and serve as the excitation light.

1.2.1 Waveguide

As shown in FIG. 1, in some embodiments, the planar waveguide 110 may comprise a core layer 112, an upper cladding layer 114, and a lower cladding layer 116. The core layer 112 may comprise a material having a refractive index of $n_2$, such as silicon-titanium oxide ($Si_xTi_{1-x}O_2$, where $0<x<1$), titanium oxide, tantalum oxide, niobium oxide, hafnium oxide, aluminum oxide, zirconium oxide, silicon nitride, aluminum nitride, titanium nitride, polycarbonate (PC), PMMA, or Su8. The upper and lower cladding layers 114 and 116 may comprise materials having a refractive index of $n_3$ and $n_4$, respectively. The materials for the upper and lower cladding layers 114 and 116 may be the same or may be different. Suitable material for the upper cladding layer 114 or the lower cladding layer 116 may comprise, for example, silicon oxide, magnesium fluoride, calcium fluoride, aluminum oxide, Su8, PMMA, or polycarbonate. The refractive index $n_2$ of the core layer 112 may be higher than the refractive indices $n_3$ and $n_4$ of the upper and lower cladding layers 114 and 116.

As noted above, for single molecule detection, one may need to prevent the excitation light from reaching the detector. In a planar waveguide, the surface of the core layer may not be as smooth as would be desired. The rough surface of the core layer may scatter part of the excitation light. It has been estimated that, for a core layer having a surface roughness of about 0.3 nm, about 0.01% excitation light may be scattered and produce the noise. In order to reduce the noise coming from surface scattering of excitation light propagating within the core, the surface roughness of the core should be less than about 0.3 nm.

1.2.2 Nanowell

Figure 2:
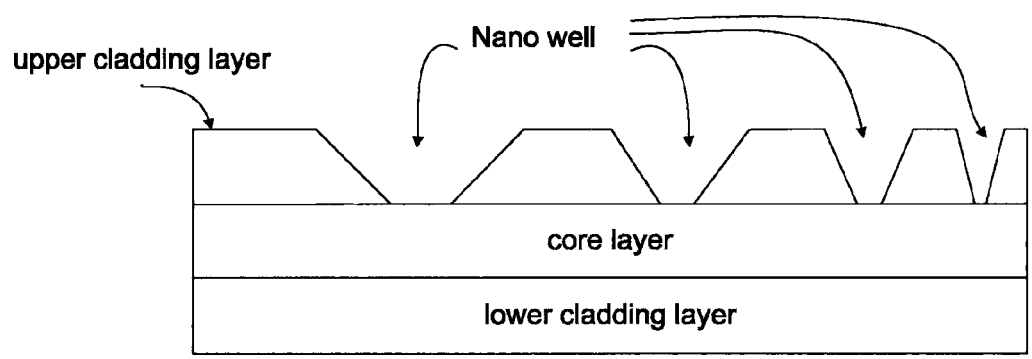
FIG. 2 is a schematic view showing nanowells of different sizes consistent with the present disclosure.

In some embodiments, at least one nanowell 120 may be formed in at least the upper cladding layer 114. The upper opening of the nanowell 120 may be larger than the bottom of the nanowell 120. The shape of the nanowell 120 is not limited. For example, the horizontal cross section of the nanowell 120 may have a circular shape, an oval shape, a rectangular shape, a square shape, or a diamond shape. As shown in FIG. 2, the size of the bottom of the nanowell 120 is also not limited. For example, the size of the bottom of the nanowell 120 may be smaller than about the wavelength of the excitation light. In some embodiments, the size of the bottom of the nanowell 120 may be smaller than about one-half, about one-quarter, or about one-eighth of the wavelength of the excitation light. As used herein, "size" may refer to diameter, length of the long axis, or length of the long side if the horizontal cross section of the nanowell 120 has a circular shape, an oval shape, or a rectangular shape. If the horizontal cross section of the nanowell 120 has a square or a diamond shape, "size" may refer to the length of the side. In one embodiment, the diameter of the upper opening of the nanowell 120 may be about 1 to about 10 μm and the diameter of the bottom of the nanowell 120 may be about 10 to about 500 nm, the angle of the sidewall of the nanowell relative to the direction perpendicular to the bottom of the nanowell may be less than about 60 degree. Such a configuration may ensure that one single molecule can enter a region near the bottom of the nanowell 120 and be detected.

Consistent with the present disclosure, part of the excitation light may enter the nanowell 120 and may, together with the spatial confinement of the nanowell 120, form an effective excitation zone 130. The effective excitation zone 130 may be formed near the bottom of the nanowell 120. When an object enters the effective excitation zone 130, it may be excited by the excitation light and emit a light to be detected by the light detector 106. Outside the effective excitation zone 130, an object may not be excited by the excitation light, or its emitted light cannot reach the light detector. It is to be understood that, the dashed line in the figure schematically illustrates the approximate upper boundary of the effective excitation zone 130, and does not limit the shape of the upper boundary of the effective excitation zone 130. For example, the upper boundary of an effective excitation zone may be in a curved shape.

Depending on different conditions, such as the position of the nanowell and/or the depth of the nanowell extending in the waveguide, a different effective excitation zone may be formed. In addition, the electromagnetic field in the effective excitation zone may be, for example, an evanescent field, a mixture of evanescent and travelling fields, or a travelling field, as described in more detail below.

Figure 3:
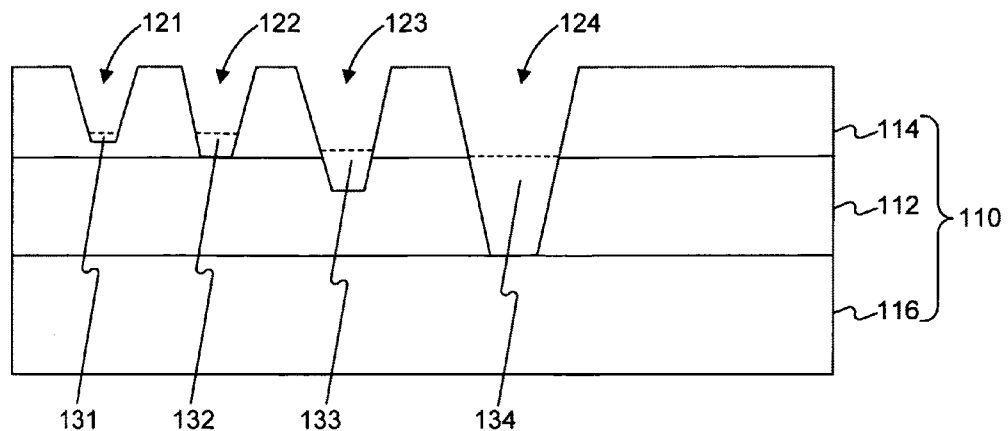
FIG. 3 is a schematic view showing different nanowell designs consistent with the present disclosure.

FIG. 3 schematically shows, as examples, different nanowell designs consistent with the present disclosure. In some embodiments, nanowell 121 may extend through partial thickness of the upper cladding layer. In some embodiments, nanowell 122 may extend through full thickness of the upper cladding layer. For nanowell 121 or 122, when the excitation light propagates in the core layer, although there may not be travelling light in the nanowell 121 or 122, part of the light travelling in the core layer may penetrate slightly into the nanowell 121 or 122. The light penetrating into the nanowell 121 or 122 may decay exponentially in the vertical direction, forming an evanescent field. This evanescent field, together with the spatial confinement of the nanowell 121 or 122, may form an effective excitation zone 131 or 132.

In some embodiments, nanowell 123 may extend through full thickness of the upper cladding layer and partial thickness of the core layer. For nanowell 123, besides an evanescent field, a travelling field component may also appear in the nanowell, forming an effective excitation zone 133.

In some embodiments, nanowell 124 may extend through full thickness of the upper cladding layer and full thickness of the core layer. For nanowell 124, most of the electromagnetic field in the nanowell may be a travelling field, and an effective excitation zone 134 is formed.

For a planar waveguide comprising nanowell 122, since the bottom end of the nanowell is located right on the upper surface of the core layer, the volume of the effective excitation zone 132 may be equal to the effective region of the evanescent field, and may be calculated approximately using the following equation:

$$V = \pi \times (D/2)^2 \times h$$

where D is the diameter of the bottom of the nanowell and h is the penetration depth of the evanescent field in the nanowell. For example, if D and h are 100 nm and 100 nm, respectively, the calculated volume of the effective excitation zone is approximately $1 \times 10^{-18}$ liter, which equals to 1 atto-liter.

In some embodiments, the surfaces of the nanowell 120 and the surface of the upper cladding layer 114 (the surface of the upper protection layer, as described in the following, if one is formed over the upper cladding layer) may possess different surface properties. The surface properties may comprise, e.g., hydrophobicity, functional group, functional group density, material density, or conductivity.

In some embodiments, the sidewall surface of the nanowell 120 may be hydrophilic, comprising a member chosen from silicon, silica, metal, or metal oxide, and the bottom surface of the nanowell 120 may be hydrophobic. However, if the bottom surface of the nanowell 120 is made of a material with hydrophilic property, it may be modified to be hydrophobic. For example, if the bottom surface of the nanowell 120 is made of silicate or metal with hydrophilic property, it may be modified to be hydrophobic using, for example, $R1_x\text{-Si}(O\text{---}R2)_{4-x}$ (where R1 is a hydrophobic group, such as alkyl chain ---$(CH_2)_n$---$CH_3$, and R2 is $C_nH_{2n+1}$, and where x is integer and $1 \le x \le 3$ and n is an integer) or using, for example, polymers with a functional group chosen from ---COOH, ---$PO_3H_2$, ---SH, or ---$NH_2$. As another example, if the bottom surface of the nanowell 120 is made of metal oxide with hydrophilic property, it may be modified to be hydrophobic using, for example, $R1_x\text{-Si}(O\text{---}R2)_{4-x}$ (where R1 is a hydrophobic group, such as alkyl chain ---$(CH_2)_n$---$CH_3$, and R2 is $C_nH_{2n+1}$, and where x is integer and $1 \le x \le 3$ and n is an integer) or using, for example, polymers with a functional group chosen from ---COOH, ---$PO_3H_2$, ---SH, or $NH_2$. By making the bottom surface of the nanowell 120 hydrophobic but keeping the sidewall surface of the nanowell 120 hydrophilic, the object being detected may be kept in the effective excitation zone near the bottom of the nanowell 120 but may not adhere to the sidewall surface of the nanowell 120. Thus, the object may be effectively excited by the excitation light entering the effective excitation zone.

In some embodiments, a plurality of nanowells may be formed in the waveguide. In some embodiments, for each of the plurality of nanowells, a light detector may be formed to detect the light emitted from an object in the effective excitation zone of the nanowell. In some embodiments, one light detector may be used to detect the light emitted from objects in the effective excitation zones of a plurality of nanowells.

1.2.3 Protection Layers

Figure 4:
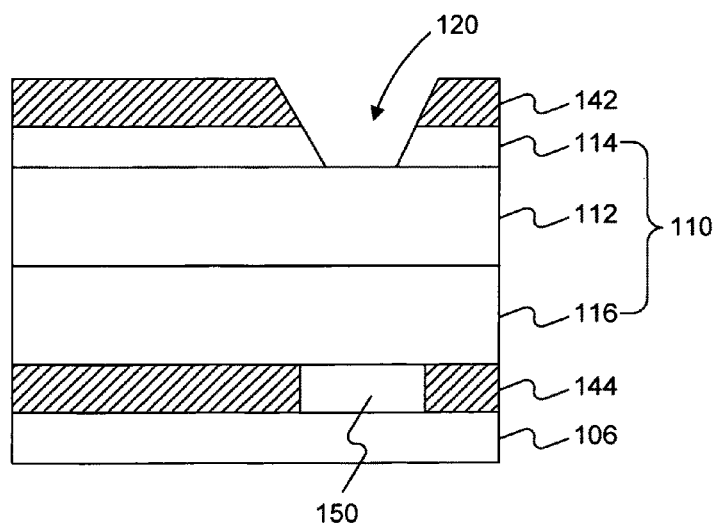
FIG. 4 is a schematic view showing a detection apparatus according to one embodiment of the present disclosure.

In some embodiments, protection layer(s) may be formed in the detection apparatus to absorb scattered excitation light and/or to block the ambient light from outside the detection apparatus, so as to increase the signal-to-noise (S/N) ratio. Referring to FIG. 4, in some embodiments, an upper protection layer 142 and a lower protection layer 144 may be formed over the upper cladding layer 114 and below the lower cladding layer 116, respectively. That is, the upper protection layer 144 may be formed on the same side of the waveguide as the nanowell 120, and the lower protection layer 144 may be formed on the opposite side of the waveguide and arranged between the lower cladding layer 116 and the light detector 106. In some embodiments, the detection apparatus may have the upper protection layer 142 formed therein. In some embodiments, the detection apparatus may have the lower protection layer 144 formed therein. In some embodiments, the detection apparatus may have both upper and lower protection layers 142 and 144 formed therein.

In some embodiments, the upper and lower protection layers 142 and 144 may be made of opaque material, such as metal or alloy. The upper and lower protection layers 142 and 144 may be made of the same material or be made of different materials. Suitable material for upper and lower protection layers 142 and 144 comprises, for example, Al, Ti, Ni, Cr, Au, Cu, Pt, or Pd, or the alloy of any two or more of them.

In some embodiments, a pinhole 150 may be formed in the lower protection layer 144 at a position below the nanowell 120. Light emitted from the object in the effective excitation zone 130 may pass through the pinhole and be detected by the light detector 106.

Figure 5:
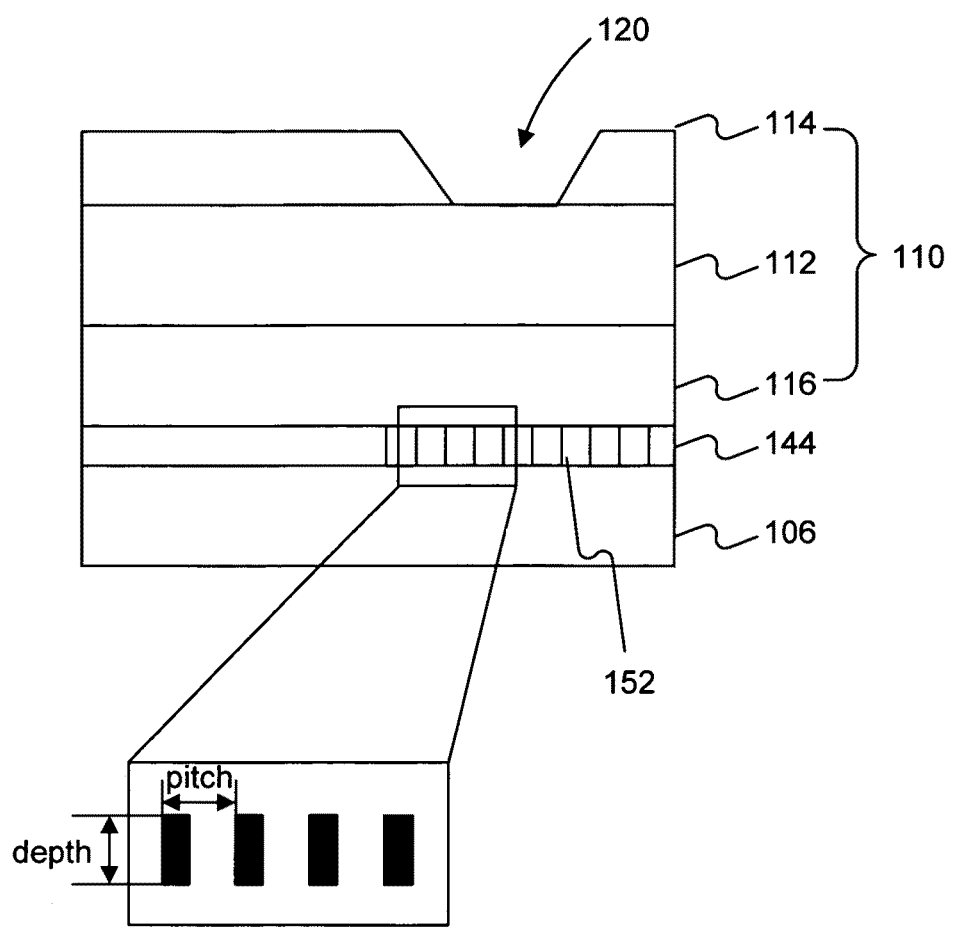
FIG. 5 is a schematic view showing a detection apparatus according to one embodiment of the present disclosure.

In some embodiments, as shown in FIG. 5, a nanostructured metal pattern 152 functioning as a grating may be arranged in the lower protection layer 144 instead of the pinhole. By properly designing the pitch and depth of the metal pattern 152, most of the light emitted from the object may pass through the metal pattern 152 but the noise originated from the excitation light may be minimized.

The light emitted from the object may be a TM mode light and the excitation light may be a TE mode light. The transmittance of a TM mode light or a TE mode light through a metal grating may depend on the pitch (i.e., grating period) and depth of the metal pattern 152. The transmittance may also depend on the refractive difference between the metal and the material surrounding the metal. Moreover, the transmittance may also depend on the angle of the light incident on the metal grating. Therefore, the S/N ratio may be further improved.

1.2.4 Light Coupler

Referring again to FIG. 1. A light coupler 104 may be arranged near the waveguide or formed on or in the waveguide. The light coupler 104 may be able to couple at least part of the incident light from the light source 102 into the waveguide 110.

Figure 6:
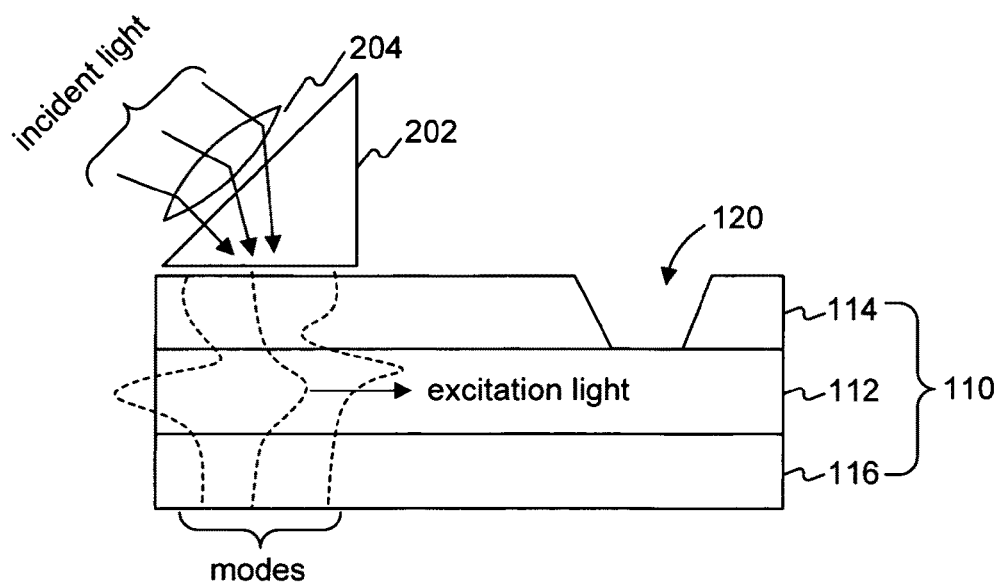
FIG. 6 is a schematic view showing a detection apparatus according to one embodiment of the present disclosure.

In some embodiments, a prism coupler may be used as the light coupler 104. As schematically shown in FIG. 6, the prism coupler may comprise a prism 202 and a collimating lens 204. The incident light emitted from the light source 102 may be focused on the same position of the waveguide 110 by the collimating lens 204. As shown in FIG. 6, part of the incident light may be coupled into the waveguide 110 by the prism coupler and propagate in the core layer 112 as the excitation light. Depending on the position of the light source and/or the incident angle of the incident light with respect to the collimating lens 204, light with different modes may be coupled into the waveguide 110 and propagate in the core layer 112, such as those shown by the dashed curves in FIG. 6. Therefore, the mode of the excitation light propagating in the waveguide may be adjustable and selectable. In some embodiments, the collimating lens 204 may be specially designed so as to expand a point light source into a linear light source, which may provide a laterally-expanded excitation light to cover larger area in the lateral direction, i.e., the direction perpendicular to the cross-section shown in FIG. 6, of the waveguide 110.

Figure 7:
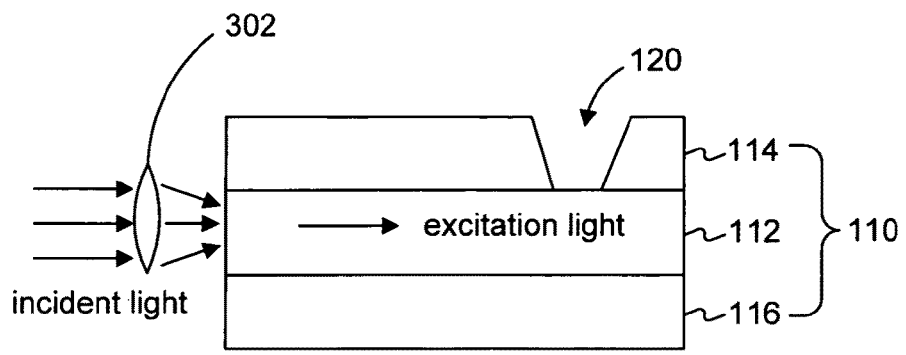
FIG. 7 is a schematic view showing a detection apparatus according to one embodiment of the present disclosure.

In some embodiments, as schematically shown in FIG. 7, a side coupler 302 may be used as the light coupler 104. The side coupler 302 may be an optical lens module. The incident light may be focused by the side coupler 302 onto and coupled into the waveguide 110, and propagate in the core layer 112 as the excitation light.

In some embodiments, a grating coupler may be used as the light coupler 104. A grating coupler is an optical component with a regular pattern, which may split and diffract light into several beams propagating in different directions. Therefore, part of the incident light may be guided into the waveguide 110 and propagate in the core layer 112 of the waveguide 110.

Figure 8:
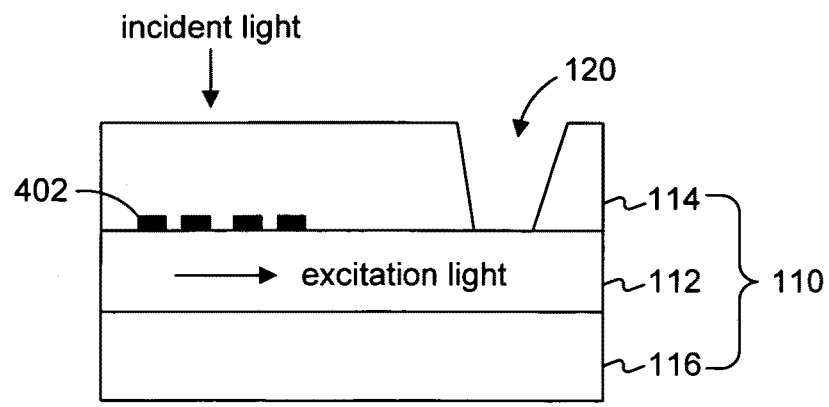
FIG. 8 is a schematic view showing a detection apparatus according to one embodiment of the present disclosure.

In some embodiments, as schematically shown in FIG. 8, the grating coupler may comprise a first grating 402 arranged at the interface between the upper cladding layer 114 and the core layer 112. Due to the interference of the light reflected from the upper and lower surface of the lower cladding layer 116, the coupling efficiency of such a grating coupler may depend on the thickness of the lower cladding layer 116.

As noted above, the incident light may not be totally coupled into the core layer 112. Part of the incident light may vertically pass through the waveguide 110 and be wasted. In some embodiments, in order to improve the coupling efficiency, a reflector (not shown) may be arranged below the waveguide 110. The reflector may reflect the light passing through the lower cladding layer 116 back to the core layer 112, causing it to be partially coupled into the core layer 112, so as to increase the total amount of light coupled into the core layer 112.

Figure 9:
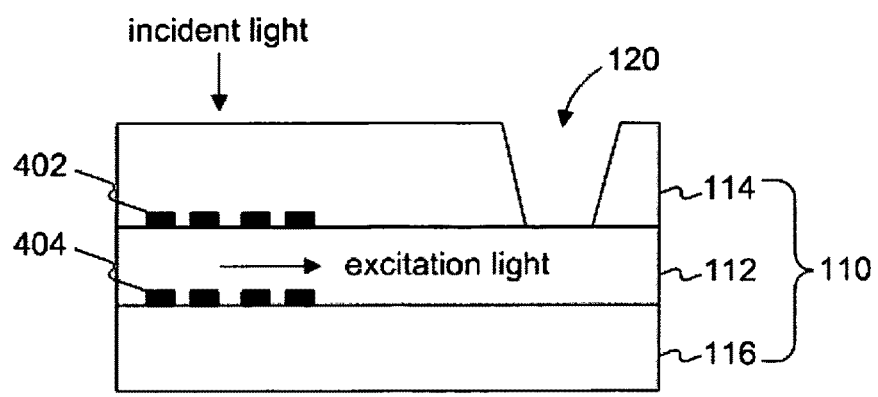
FIG. 9 is a schematic view showing a detection apparatus according to one embodiment of the present disclosure.
Figure 10:
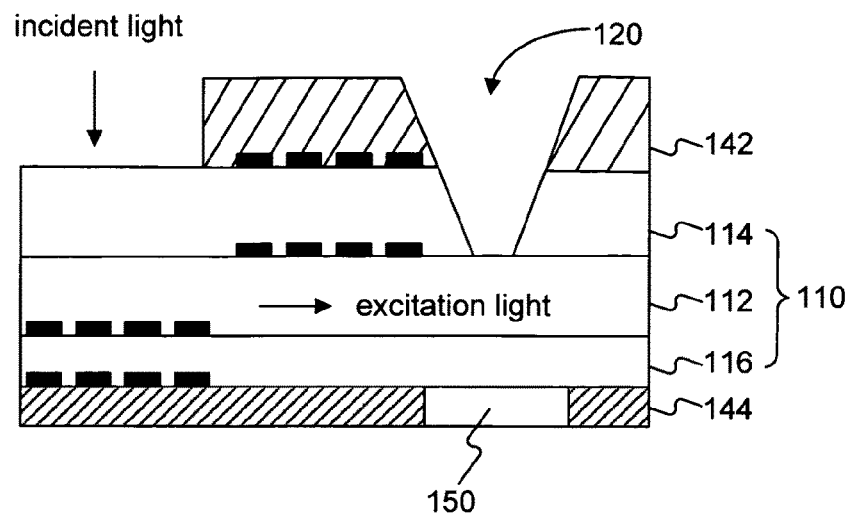
FIG. 10 is a schematic view showing a detection apparatus according to one embodiment of the present disclosure.

In some embodiments, the grating coupler may further comprise a second grating 404 arranged at the interface between the core layer 112 and the lower cladding layer 116, as shown in FIG. 9. The second grating 404 may be arranged right below the first grating 402. In some embodiments, the coupling efficiency may be further increased by adding more gratings. For example, if the detection apparatus comprises upper and lower protection layers, gratings may also be arranged at the interfaces between the protection layers and the cladding layers, as schematically shown in FIG. 10.

In some embodiments, a portion of the upper cladding layer 114 may be removed to expose the core layer 112. A grating, such as grating 406 shown in FIG. 11, may be arranged on the exposed portion of the core layer 112.

The shape of the grating may not be limited to that shown in FIGS. 8-11. For example, to increase the coupling efficiency, in some embodiments, a grating with curved structure may be used, such as blaze grating or multi-level grating, where multi-level grating simulates the blaze grating by dividing the blaze into several steps.

Figure 12:
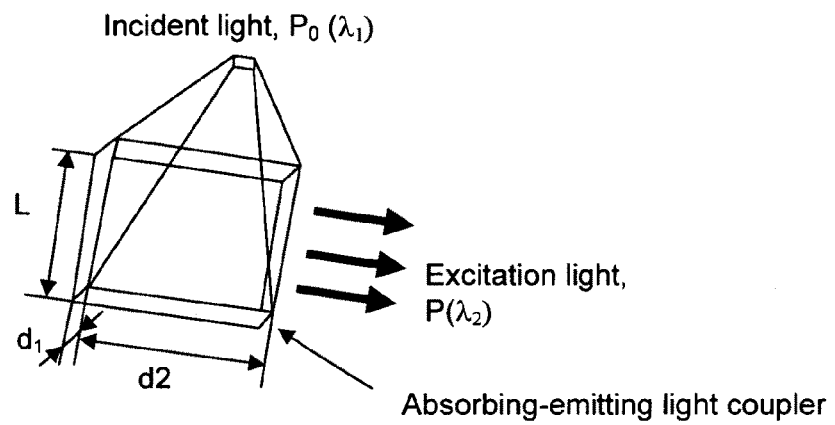
FIG. 12 shows an absorbing-emitting light coupler consistent with the present disclosure.

In some embodiments, the light may also be indirectly coupled into the waveguide 110 using an absorbing-emitting light coupler. FIG. 12 schematically shows an absorbing-emitting light coupler. The absorbing-emitting light coupler may comprise a photoluminescent layer, which may absorb the incident light and emit a fluorescent light with a longer wavelength. Light emitted by the light source may be incident on the upper surface of the absorbing-emitting light coupler, and the fluorescent light may be emitted from the side of the absorbing-emitting light coupler. Part of the fluorescent light may be coupled into the waveguide and propagate in the core layer of the waveguide as the excitation light to excite the object. The power coupling efficiency may be calculated as follows:

$$P(\lambda_2)/P_0(\lambda_1)=(1-T_1)(1+R_1T_1)\times\phi_{FL}\times T_2\times\eta_c\times T_3$$

where $\lambda_1$ and $\lambda_2$ are the wavelengths of the incident light and light emitted from the side of the absorbing-emitting light coupler, respectively. $P_0(\lambda_1)$ and $P(\lambda_2)$ are the power of the incident light and the power of the light coupled into the core layer 112 of the waveguide 110, respectively. $R_1$ is the reflectivity at the interface between the absorbing-emitting light coupler and the lower cladding layer 116. $T_1$ is the transmittance of a light with a wavelength of $\lambda_1$ in the absorbent layer after travelling a distance of $d_1$ and $T_2$ is the transmittance of a light with a wavelength of $\lambda_2$ in the absorbent layer after travelling a distance of $d_2$. $\phi_{FL}$ is the photoluminescence quantum yield of the photoluminescence material. $\eta_c$ is the coupling efficiency of the absorbing-emitting light coupler. $T_3$ is the transmittance of the light emitted from the absorbing-emitting light coupler passing through the waveguide with a total length of $d_3$.

For an absorbing-emitting light coupler, since the area of the side surface is much smaller than the area of the upper surface, the power intensity of the light emitted from the absorbing-emitting light coupler and coupled into the core layer 112 may be much higher than that of the light incident on the absorbing-emitting light coupler.

The photoluminescence material used in the absorbing-emitting light coupler may be selected based on the Stokes shift. For example, the photoluminescence material may have a Stokes shift of equal to or larger than about 30 nm. In some embodiments, the photoluminescence material may be photoluminescence dyes, such as anthracene, coumarin, pyrene, stilbene, porphyrin, perylene, Alq3, eosin, Bodipy dyes, fluorescein, rhodamine, polymethine dye, DCM or its derivatives. In some embodiments, the photoluminescence material may be photoluminescence polymers, such as PPV or its derivatives. In some embodiments, the photoluminescence material may be inorganic material, such as quantum dots, alumina oxide, or zinc oxide.

Figure 13:
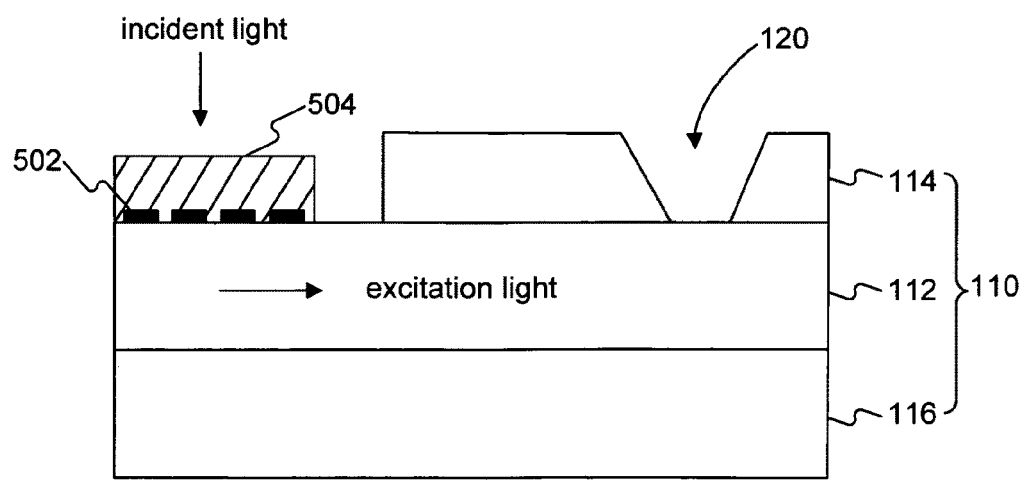
FIG. 13 is a schematic view showing a detection apparatus according to one embodiment of the present disclosure.
Figure 14:
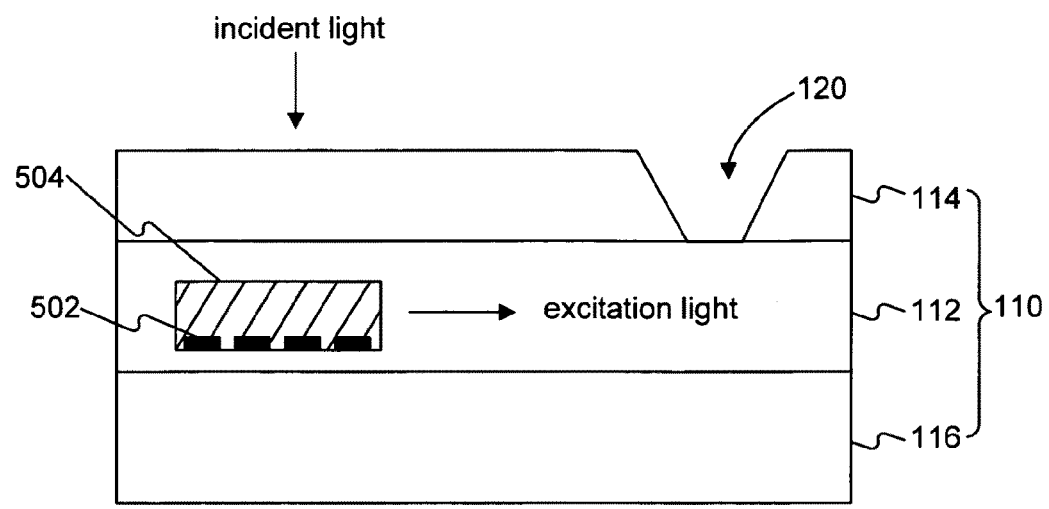
FIG. 14 is a schematic view showing a detection apparatus according to one embodiment of the present disclosure.

In some embodiments, the coupling efficiency may be increased by combining the grating with the absorbing-emitting light coupler. The combined light coupler may comprise a grating 502 and an absorbing-emitting material 504. In some embodiments, as shown in FIG. 13, the combined light coupler may be arranged on the surface of an exposed portion of the core layer 112. In some embodiments, as shown in FIG. 14, the combined light coupler may be arranged within the core layer 112. The grating may help to increase the path length of the incident light travelling in the absorbing-emitting material, so as to increase the amount of light being absorbed by the absorbing-emitting material and thus the photoluminescence efficiency. Therefore, more incident light may be converted to the excitation light and the power coupling efficiency may be increased.

1.2.5 Other Optional Components of the Apparatus

Figure 15:
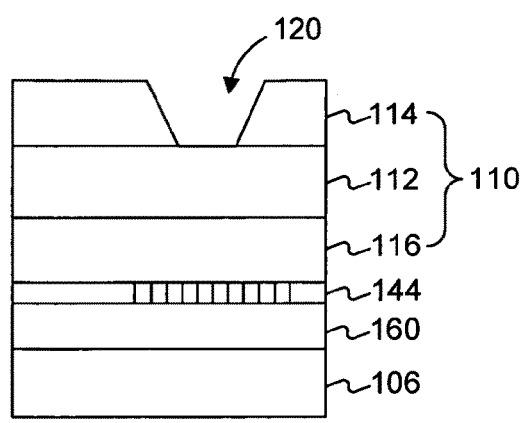
FIG. 15 is a schematic view showing a detection apparatus according to one embodiment of the present disclosure.
Figure 16A:
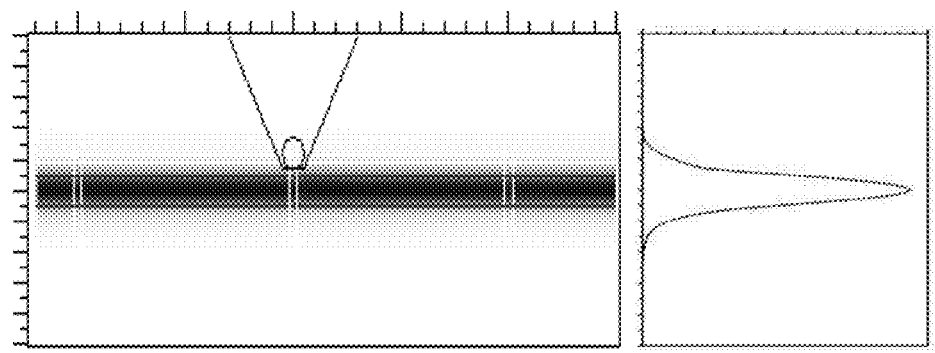
FIGS. 16A-16D show the computer-simulation results for different nanowells.
Figure 16B:
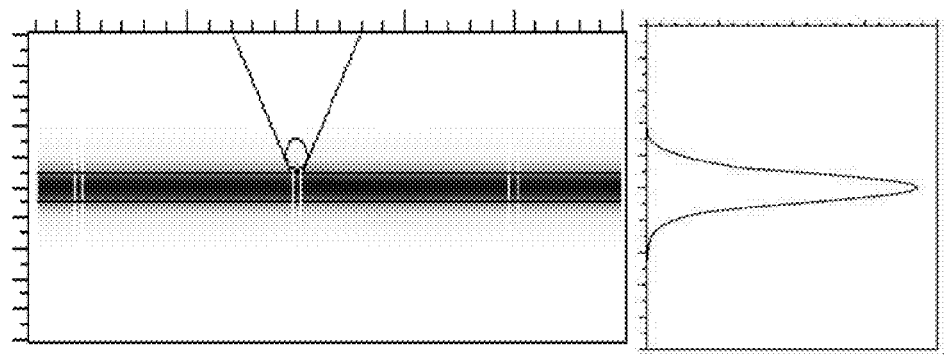
Figure 16C:
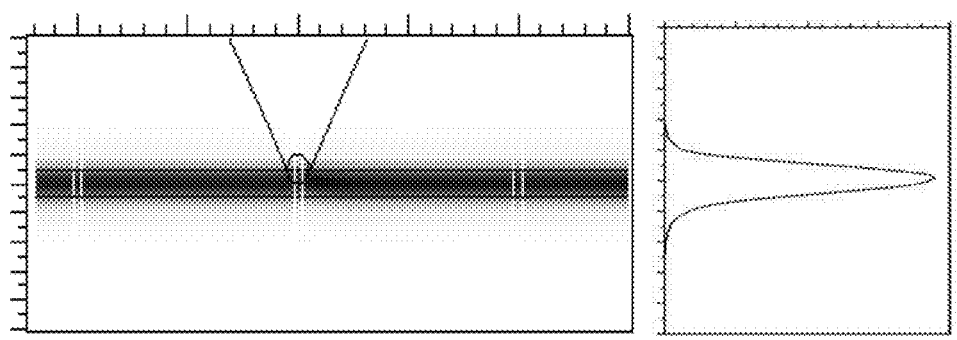
Figure 16D:
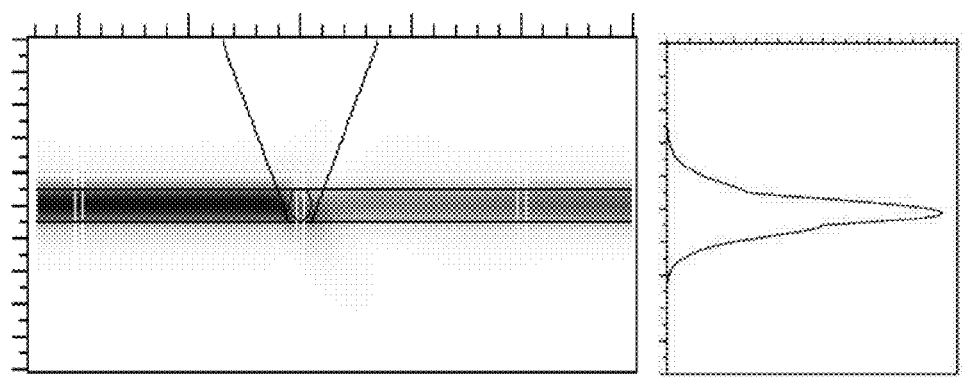

In some embodiments, as shown in FIG. 15, an optical filter 160 may be arranged between the lower protection layer 144 and the light detector 106. In some embodiments, the optical filter 160 may be arranged between the lower cladding layer 116 and the detector 106 without the lower protection layer 144. In some embodiments, the lower protection layer 144 itself may serve as an optical filter. An optical filter may allow a light with a wavelength within a certain range to pass through but at least partially block a light with a wavelength outside the certain range. Therefore, by properly choosing the optical filter 160, it may allow the light emitted from the object to pass through but reduce the noise caused by the excitation light, so as to improve the S/N ratio.

Consistent with the present disclosure, the object may be contained in a sample solution, which may be filled in the nanowell 120. In some embodiments, a microfluidic channel (not shown) may be used to conduct the sample solution into the nanowell 120. The microfluidic channel may be designed in a way that the target objects passes through the nanowell one at a time, so as to realize a flow-cytometry-like detection. In some embodiments, a cover (not shown) may be formed over the waveguide to hold the sample solution and/or to block the ambient light.

In some of the above-described figures schematically showing the structures of detection apparatuses consistent with the present disclosure, for simplicity, some components are not shown. For example, FIG. 6 shows the waveguide 110, the nanowell 120, and the prism coupler comprising prism 202 and collimating lens 204. Other components of the detection apparatus are not shown. It is to be understood that the detection apparatuses shown in these figures may also comprise other components as disclosed herein. For example, the detection apparatus shown in FIG. 6 may also comprise the light detector, the cover, the protection layer(s), and/or the optical filter.

2. METHODS OF DETECTION AND APPLICATIONS OF THE PRESENT DISCLOSURE

In another aspect, the disclosure relates to a method of detecting an object, such as a single-molecule object, using the detection apparatus as disclosed herein. Consistent with the present disclosure, a sample solution comprising the object may be filled in the nanowell 120 formed in the waveguide 110 of the detection apparatus. An incident light emitted by a light source may be partially coupled by a light coupler into the waveguide 110 and propagate in the core layer 112 of the waveguide 110. The light coupled into the waveguide 110 may serve as an excitation light. The object, when entering the effective excitation zone, may be excited by the excitation light and emit a light to be detected by a light detector.

The detection apparatuses and systems consistent with the present disclosure, and method of using the same may be applied to, e.g., nucleic acid detection, DNA sequencing, biomarker identification, or flow cytometry. The detection apparatuses can detect and process low intensity light signal, which makes single molecule object detection possible.

2.1 Labels for Use with the Apparatus

In some embodiments of the methods of the present disclosure, labels are attached to the analyte(s) (i.e., the substance(s) to be detected), the probe(s), such as primers, antibodies, or other reagents that interact with the analyte(s), or other reagent(s), such as nucleotides (including nucleotide analogs). Any label can be used on the analyte or probe which can be useful in the correlation of signal with the amount or presence of analyte.

For example, a wide variety of fluorescent molecules can be utilized in the present disclosure including small molecules, fluorescent proteins and quantum dots. Useful fluorescent molecules (fluorophores) include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AFPs-AutoFluorescent Protein-(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodaminelsoThioCyanate); True Blue; Tru Red; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), also covering a wide spectrum such as Cy3, Cy3B, Cy3.5, Cy5, Cy5.5, Cy7; members of the Oyster dye fluorophores (Denovo Biolabels) such as Oyster-500, -550, -556, 645, 650, 656; members of the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521 XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor series or Quasar series of dyes (Biosearch Technologies) such as CAL Fluor Gold 540, CAL Fluor Orange 560, Quasar 570, CAL Fluor Red 590, CAL Fluor Red 610, CAL Fluor Red 635, Quasar 670; quantum dots, such as quantum dots of the Evi-Tags series (Evident Technologies) or quantum dots of the Qdot series (Invitrogen) such as the Qdot 525, Qdot565, Qdot585, Qdot605, Qdot655, Qdot705, Qdot 800; fluorescein; rhodamine; and/or phycoerythrin; or combinations thereof. See, e.g., U.S. Application Publication 2008/0081769.

In some embodiments, at least one bioluminescent or chemiluminescent system is provided which generates light in the presence of an entity such as an analyte, reagent, or reaction product. For example, a bioluminescent or chemiluminescent system can be used to detect pyrophosphate generated in a sequencing by synthesis reaction (discussed in more detail below); to detect the presence of metals such as iron or copper by their catalysis of a light-generating reaction; or to measure the amount of a reagent bound by an analyte, wherein the reagent comprises at least one component of the bio- or chemi-luminescent system.

Examples of bioluminescent systems known in the art include systems comprising at least one luciferase, e.g., firefly luciferases, including *Photinus pyralis* luciferase. A bioluminescent system can be used to detect pyrophosphate, for example, by providing luciferase, ATP sulfurylase, luciferin, and adenosine 5' phosphosulfate, together with the components of the sequencing by synthesis reaction (in which dATP can be substituted with an analog such as dATPαS to avoid nonspecific light due to consumption of dATP by luciferase). When pyrophosphate is generated by a nucleotide incorporation event, ATP sulfurylase produces ATP in an adenosine 5' phosphosulfate dependent manner. The ATP drives conversion of luciferin to oxyluciferin plus light by luciferase. Other bioluminescent systems include systems based on photoproteins such as aequorin, which oxidizes coelenterazine to excited coelenteramide, which emits light.

Examples of chemiluminescent systems include luminol plus hydrogen peroxide, which can undergo a light-emitting reaction in the presence of a metal catalyst or auxiliary oxidant; diphenyl oxalate plus hydrogen peroxide and a suitable dye, which undergoes excitation and light emission in a multistep reaction that produces carbon dioxide (examples of suitable dyes include phenylated anthracene derivatives such as 9,10-diphenylanthracene, 9,10-Bis(phenylethynyl)anthracene, and 1-Chloro-9,10-bis(phenylethynyl)anthracene, and rhodamines such as rhodamine 6G and rhodamine B); singlet oxygen-producing systems such as hydrogen peroxide plus sodium hypochlorite; and systems comprising an enzyme such as horseradish peroxidase, which acts on luminol or other commercially available substrates.

In some embodiments, the methods of the present disclosure comprise forming covalent attachments, such as between reagents or analytes and labels, or between a reagent, such as a polymerase used in a sequencing reaction, and a surface, such as the surface of a nanowell. Many methods for forming covalent attachments, such as of reagents to labels and/or surfaces, are known in the art. Non-covalent attachment methods can also be used. A number of different chemical modifiers can be used to facilitate attachment formation. Examples of chemical modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. In some embodiments, attachments are formed between two entities by using an appropriate combination of modifiers (e.g., an electrophilic modifier and a nucleophilic modifier), wherein each entity comprises at least one modifier.

In some embodiments, attachments are formed between two entities by using a chemical modifier present on one of the entities and a naturally occurring moiety, for example, an amine or sulfhydryl, of the other entity. In some embodiments, modifiers that are reactive to amines are used. An advantage of this reaction is that it can be fast and can avoid production of toxic by-products. Examples of such modifiers include NHS-esters, aldehydes, epoxides, acyl halides, and thio-esters. Most proteins, peptides, glycopeptides, etc., have free amine groups, which can react with such modifiers to link them covalently to these modifiers. Nucleic acid probes with internal or terminal amine groups can also be synthesized, and are commercially available (e.g., from IDT or Operon). Thus, biomolecules can be bound (e.g., covalently or non-covalently) to labels or other reagents using similar chemistries.

A number of other multi-functional cross-linking agents can be used to convert the chemical reactivity of one kind of modifier to another. These groups can be bifunctional, tri-functional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS-Y-NHS, is a homo-bi-functional cross-linker and could connect two entities that each comprise an amine. If X is NHS-ester and Z is a maleimide group, the resulting cross-linker, NHS-Y-maleimide, is a hetero-bi-functional cross-linker and could link an entity comprising an amine with an entity comprising a thio-group. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-di-ols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc.

Other modifier alternatives (such as photo-crosslinking and thermal crosslinking) are known to those skilled in the art. Commercially available technologies include, for example, those from Mosiac Technologies (Waltham, Mass.), EXIQON™ (Vedbaek, Denmark), Schleicher and Schuell (Keene, N.H.), Surmodics™ (St. Paul, Minn.), XENOPORE™ (Hawthorne, N.J.), Pamgene (Netherlands), Eppendorf (Germany), Prolinx (Bothell, Wash.), Spectral Genomics (Houston, Tex.), and COMBIMATRIX™ (Bothell, Wash.).

2.2 Nucleic Acid Detection

A detection apparatus consistent with the present disclosure may be used as part of a system for or in methods or processes of molecule detection, e.g., nucleic acid sequencing. This apparatus, and methods or processes utilizing it, are useful for, e.g., analytical and diagnostic applications. These applications may be private, public, commercial, or industrial.

A detection apparatus consistent with the present disclosure may be used with a wide variety of sequencing modalities and may be suitable for sequencing single molecules. Additionally, the detection apparatus consistent with the present disclosure have simplified design, assembly, and production relative to existing biochip devices.

A detection apparatus consistent with the present disclosure may be used as part of a system for or in methods and processes of biomolecule detection, including nucleic acid hybridization or sequencing for, e.g., whole genome sequencing, transcriptional profiling, comparative transcriptional profiling, or gene identification. Biomolecule detection can also include detection and/or measurement of binding interactions, e.g., protein/protein, antibody/antigen, receptor/ligand, and nucleic acid/protein. These applications are useful for analytical or diagnostic processes and methods.

2.2.1 Molecules to be Detected

Nucleic acids suitable for detection by the methods provided by the present disclosure may include any nucleic acid, including, for example, DNA, RNA, or PNA (peptide nucleic acid), and may contain any sequence—both known and unknown, including naturally occurring or artificial sequences. The nucleic acid may be naturally derived, recombinantly produced, or chemically synthesized. The nucleic acid may comprise naturally-occurring nucleotides, nucleotide analogs not existing in nature, or modified nucleotides. The length of the nucleic acid to be detected may vary based on the actual application. In some embodiments, the nucleic acid may include at least 10, 20, 50, 100, 200, 500, 1000, 2000, 5000, 10000, 20000 bases, or more. In some embodiments, the nucleic acid may be from 10 to 20, from 10 to 50, from 10 to 100, from 50 to 100, from 50 to 500, from 50 to 1000, from 50 to 5000, from 500 to 2000, from 500 to 5000, or from 1000 to 5000 bases.

A nucleic acid may be single-stranded for detection. Single stranded nucleic acid templates may be derived from a double stranded molecule by means known in the art including, for example, heating or alkali or other chemical treatment. Single stranded nucleic acid templates may also be produced by, e.g., chemical or in vitro synthesis.

In some embodiments, the nucleic acid to be detected may be circular. In some embodiments, the methods of the present disclosure comprise providing a circular nucleic acid molecule comprising an insert with a known sequence, which can be used as a binding site for a primer. The circular nucleic acid molecule can be provided in a single or double stranded state, and will generally comprise at least one covalently closed strand. Double stranded circular molecules may comprise a nicked strand or a second covalently closed strand.

In some embodiments, the circular nucleic acid molecule is provided by isolating it in circular form from its source, if part of its sequence is known and thus can serve as the nucleic acid insert (e.g., a conserved motif within the sequence of a gene contained in the circular molecule may be known, or the molecule may be known to contain a sequence based on its ability to hybridize under high stringency conditions to another nucleic acid of known sequence). In some embodiments, the sequence of the nucleic acid insert is known only inexactly, as would be the case when knowledge of the sequence is derived from stringent hybridization properties. In some embodiments, the sequence of the nucleic acid insert is known exactly, such as would be the case when the circular nucleic acid molecule has a known backbone sequence or has been engineered to contain a known sequence.

In some embodiments, the circular nucleic acid molecule is provided by performing an in vitro reaction or reactions to incorporate a linear nucleic acid sample into a circular molecule along with a nucleic acid insert. The in vitro reaction or reactions can in some embodiments comprise ligation by a ligase and/or other strand joining reactions such as can be catalyzed by various enzymes, including recombinases and topoisomerases. DNA ligase or RNA ligase may be used to enzymatically join the two ends of a linear template, with or without an adapter molecule or linkers, to form a circle. For example, T4 RNA ligase couples single-stranded DNA or RNA, as described in Tessier et al., *Anal Biochem,* 158: 171-78 (1986). CIRCLIGASE™ (Epicentre, Madison, Wis.) may also be used to catalyze the ligation of a single stranded nucleic acid. Alternatively, a double stranded ligase, such as *E. coli* or T4 DNA ligase, may be used to perform the circularization reaction.

In some embodiments, providing the circular nucleic acid molecule comprises replicating a nucleic acid template by extending from at least one primer (which can include random primers with 5' flaps of known sequence that can serve as the nucleic acid insert) comprising complementary regions and circularizing the amplified nucleic acid, such as may be catalyzed by a ligase or a recombinase; the amplified nucleic acid may in some embodiments be processed at its ends, e.g., by restriction or phosphorylation, prior to circularization.

In some embodiments, the circular nucleic acid molecule is provided by performing chemical circularization. Chemical methods employ known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. The ends of a linear template may also be joined by condensing a 5'-phosphate and a 3'-hydroxyl, or a 5'-hydroxyl and a 3'-phosphate.

In some embodiments, the circular nucleic acid molecule contains an insert sequence that could be considered an end link primer (discussed below) except that it is not at an end, since the molecule is circular.

2.2.1.1 End Link Primer

In some embodiments, a linear nucleic acid may further comprise one or more end link primers coupled to the 5' end, the 3' end, or both the 5' end and the 3' end of the nucleic acid. In particular embodiments, an end link primer may be affixed to the 3' end of the nucleic acid. End link primers may be used to provide a complementary sequence for one or more detecting primers, e.g., a sequencing primer.

End link primers are short nucleic acid molecules usually composed of less than 100 nucleotides. In some embodiments, the end link primer may be at least 5, 10, 15, 20, 25, 30, 50, 75, 90 nucleotides, or more, in length. In certain embodiments, end link primers may be from 8 to 25, from 10 to 20, from 10 to 30, or from 10 to 50 nucleotides in length. In some embodiments, the end link primers may be unbranched, however, in other embodiments, they may be branched.

The end link primer may serve as a complement to one or more primers used to detect the nucleic acid, e.g., a sequencing primer. In some embodiments, the primer may be used to detect the nucleic acid by hybridization, e.g., the primer may contain a detectable label, e.g., a fluorescent label. In some embodiments, the 5' end of the end link primer may comprise a sequence complementary to a sequencing primer. In some embodiments, the end link primer sequence that is complementary to the sequencing primer may be oriented so that the 3' end of the sequencing primer may be immediately adjacent to the first nucleotide in the nucleic acid to be sequenced.

In some embodiments, end link primers may be added to ends of the nucleic acid to be detected by a ligase, for example, a DNA ligase. In some embodiments, the end link primer and nucleic acid to be detected may be both single stranded before the ligation. In other embodiments, both may be double stranded. In still other embodiments, one may be single stranded and the other may be double stranded. Ligation is well known in the art. For example, in the polony sequencing method, Shendure et al. (*Science,* 309:1728-1732 (2005)) ligated a T30 end link primer (32 bp) to a sample DNA segment with the New England Biolabs' (NEB) Quick Ligation kit. There, the ligation reaction solution included 026 pMole of DNA, 0.8 pMole of T30 end link primer, 4.0 μl T4 DNA Ligase, in 1× Quick Ligation Buffer. After mixing, the reaction solution was incubated for about 10 minutes at room temperature, and then placed on ice. The ligation reaction was stopped by heating the samples to 65° C. for 10 minutes.

In other embodiments, the end link primer may be synthesized on the nucleic acid to be detected. For example, the end link primer may be a homopolymer added by, e.g., terminal transferase. For example, Harris et al., (*Science* 320:106-109 (2008)) added a poly A tail to DNA templates, which served as the complement to a poly T sequencing primer in the single molecule sequencing of a viral genome.

2.2.1.2 Sequencing Primer

A sequencing primer is a single-stranded oligonucleotide complementary to a segment of the nucleic acid to be detected or its associated end link primer. In some embodiments, the sequencing primer may be at least 8, 10, 15, 20, 25, 30, 35, 40, 45, 50 nucleotides, or more in length. In particular embodiments, the sequencing primer may be from 8 to 25, from 10 to 20, from 10 to 30, or from 10 to 50 nucleotides in length. The sequencing primer may be made up of any type of nucleotide, including naturally-occurring nucleotides, nucleotide analogs not existing in nature, or modified nucleotides.

In some embodiments, a sequencing primer may contain modified nucleotides, e.g., locked nucleic acids (LNAs; modified ribonucleotides, which provide enhanced base stacking interactions in a polynucleic acid). As an illustration of the utility of LNAs, Levin et al. (Nucleic Acid Research 34(20):142 (2006)) showed that a LNA-containing primer had improved specificity and exhibited stronger binding relative to the corresponding unlocked primer. Three variants of the MCP1 primer (5'-cttaaattttcttgaat-3') containing 3 LNA nucleotides (in caps) at different positions in the primer were made: MCP1-LNA-3'(5'-cttaaattttCtTgaAt-3'); MCP1-LNA-5' (5'-CtTaAattttcttgaat-3'); and MCP1-LNA-even (5'-ct-TaaatTttctTgaat-3'). All LNA-substituted primers had enhanced Tm, while the MCP1-LNA-5' primer exhibited particularly enhanced sequencing accuracy (Phred Q30 counts). Accordingly, in particular embodiments, the sequencing primer may contain at least one locked nucleotide in its 5' region, i.e., the 5' half, third, or quarter of the sequencing primer.

Sequencing primers and single stranded sample nucleic acids (i.e., a nucleic acid to be detected including at least one end link primer) may be hybridized before being applied to a detection apparatus consistent with the present disclosure. The sequencing primer and sample nucleic acid may be hybridized by mixing the sample nucleic acid with a molar excess of sequencing primer in a salt-containing solution, such as 5×SSC (or 5×SSPE), 0.1% Tween 20 (or 0.1% SDS), and 0.1% BSA buffer. The mixture may be heated to 65° C. for at least 5 minutes and slowly cooled to room temperature, to allow primer/template annealing. Residual primers may be eliminated by appropriate means including, e.g., a molecular sieve.

Primers, including both end link and sequencing primers, may be designed by appropriate means, including visual inspection of the sequence or computer-assisted primer design. Numerous software packages are available to assist in the primer design, including DNAStar™ (DNAStar, Inc., Madison, Wis.), OLIGO 4.0 (National Biosciences, Inc.), Vector NTI® (Invitrogen), Primer Premier 5 (Premierbiosoft), and Primer3 (Whitehead Institute for Biomedical Research, Cambridge, Mass.). Primers may be designed taking into account, for example, the molecule to be sequenced, specificity, length, desired melting temperature, secondary structure, primer dimers, GC content, pH and ionic strength of the buffer solution, and the enzyme used (i.e., polymerase or ligase). See, e.g., Joseph Sambrook and David Russell, *Molecular Cloning: A Laboratory Manual* Cold Spring Harbor Laboratory Press; 3rd edition (2001).

2.2.2 Sequencing Modalities

Some embodiments of the present disclosure are methods of sequencing a nucleic acid, comprising the steps of (a) providing a detection apparatus comprising: a waveguide comprising: a core layer; and a first cladding layer; at least one nanowell formed in at least the first cladding layer; and a detector; (b) providing at least one nucleic acid molecule; (c) locating the at least one nucleic acid molecule individually within the at least one nanowell; (d) performing single molecule sequencing-by-synthesis of the at least one nucleic acid molecule, wherein the single molecule nucleic acid sequencing-by-synthesis leads to emission of light correlated to the identity of at least one base in the nucleic acid; (e) detecting the light with the detector, resulting in an output signal; and (f) processing the output signal to determine an identity of at least one base in the nucleic acid.

In these methods, "locating the at least one nucleic acid molecule individually within the at least one nanowell" is understood to mean that a single nucleic acid molecule is located in a nanowell, i.e., there is at least one nanowell in which one (and not more than one) nucleic acid molecule is located. In some embodiments, there are a plurality of nanowells which each individually contains one (and not more than one) nucleic acid molecule. In some embodiments, during operation, some of the plurality of nanowells contain nucleic acid molecules and others do not. That is, the concentration of nucleic acid molecules in the sample solution is lower than a certain value so that not all nanowells have nucleic acid molecules contained in them. This may prevent the scenario that two or more molecules enter the same nanowell successively before a sequencing is completed, so as to prevent the results of one sequencing from comprising information from more than one molecules. For example, in some embodiments of the present disclosure, less than or equal to 50%, 40%, 30%, 25%, 20%, 15%, 10%, 9%, 8%, 7%, 6%, 5%, 4%, 3%, 2%, or 1% of the nanowells will generate a signal due to the low concentration of the biological molecules to be detected or identified.

In some embodiments, the concentration of the nucleic acid molecules in the sample solution may depend on the volume of the effective excitation zone. For example, if the volume of the effective excitation zone is 1 atto-liter, the concentration of the nucleic acid molecules in the sample solution may be about 1.6 μM. In some embodiments, the optimum concentration of the nucleic acid molecules in the sample solution may be from about 1-100 μM to about 1-100 μM.

In some embodiments, the nucleic acid molecules to be detected are provided at a concentration that is substoichiometric relative to the volume of the effective excitation zone of the nanowells of an apparatus according to the disclosure. For example, if the effective excitation zone is 1 atto-liter, nucleic acid molecules can be provided at a concentration ranging from 0.01 to 0.5 molecules per atto-liter, 0.05 to 0.2 molecules per atto-liter, or about 0.1 molecules per atto-liter. The concentrations can be scaled appropriately based on the effective excitation zone size. In some applications, it may be desirable to use higher or lower concentrations based on factors such as the relative importance of minimizing multiple signals from the same nanowell versus generating signal from a larger proportion of nanowells.

In some embodiments, the nucleic acid molecules to be detected are provided at a concentration that is in stoichiometric equivalence or excess relative to the volume of the effective excitation zone of the nanowells of an apparatus according to the disclosure. For example, if the effective excitation zone is 1 atto-liter, nucleic acid molecules can be provided at a concentration ranging from 1 to 50 molecules per atto-liter, 2 to 20 molecules per atto-liter, or 3 to 10 molecules per atto-liter. Use of these concentration ranges can be paired with provision of the enzyme for sequencing the nucleic acid molecules at a substoichiometric level, for example, 0.01 to 0.5 active, accessible polymerases per nanowell, 0.05 to 0.2 active, accessible polymerases per nanowell, or about 0.1 active, accessible polymerases per nanowell.

Attachment of enzymes to be used for sequencing or other detection reactions to a surface of a nanowell can result in some enzymes being rendered inaccessible, inactive, or both due to factors such as the location of the attachment and whether the structure of the enzyme is affected. The number of active, accessible polymerases per nanowell can be estimated empirically by providing the other components of a positive control sequencing-by-synthesis reaction in excess and observing how many nanowells generate fluorescent signals consistent with the presence of active, accessible enzyme. When a large fraction, such as 50% or more of the nanowells, generate fluorescent signal, a random distribution model would estimate that many of the nanowells contain at least two active, accessible enzymes (e.g., when 50% of the wells generate signal, about 25% of the wells are expected to contain at least two active, accessible enzymes). In such a situation, it can be advisable to limit the concentration of the nucleic acid molecule to be sequenced in order to minimize the frequency of two different sequencing complexes forming in the same nanowell. Alternatively, when a small fraction, such as 10% or less of the nanowells, generate fluorescent signal, a random distribution model would estimate that few of the nanowells contain at least two active, accessible enzymes (e.g., when 10% of the wells generate signal, about 1% of the wells are expected to contain at least two active, accessible enzymes). In such a situation, it can be advisable to use a relatively high concentration of the nucleic acid molecule to be sequenced in order to minimize the frequency of no sequencing complexes forming in a nanowell that does have an accessible, active enzyme.

In some embodiments, the single molecule nucleic acid sequencing-by-synthesis leads to emission of light via chemiluminescence. Notably, in these embodiments, it is not necessary for the apparatus to comprise a light source, as chemiluminescence generates light from chemical energy.

In some embodiments, the apparatus further comprises a light source, which may be used to provide excitatory light, e.g., for causing the single molecule nucleic acid sequencing-by-synthesis to emit light via fluorescence.

The detection apparatuses and methods provided by the present disclosure may be used to detect and sequence nucleic acids by means known in the art, as reviewed in, e.g., U.S. Pat. No. 6,946,249 and Shendure et al., *Nat. Rev. Genet.* 5:335-44 (2004). The sequence modalities can be chosen from single molecule sequencing methods known in the art. In some embodiments, the sequencing methods may rely on the specificity of either a DNA polymerase or DNA ligase and may include, e.g., base extension sequencing (single base stepwise extensions) and multi-base sequencing by synthesis (including, e.g., sequencing with terminally-labeled nucleotides). The methods typically involve providing a sample nucleic acid, which may include at least one end link primer. The nucleic acid may be provided in single stranded form or may be rendered single stranded, e.g., by chemical or thermal denaturation. Sequencing may be then initiated at a sequencing primer.

In some embodiments, the methods of the present disclosure comprise forming covalent attachments, such as between reagents or analytes and surfaces or labels. For example, in single molecule sequencing procedures, a nucleic acid molecule or an enzyme such as a polymerase may be attached to the bottom of the nanowell. Such an attachment can allow the acquisition of data over multiple sequencing cycles. Many methods for forming covalent attachments, such as of reagents to surfaces or labels, are known in the art. Non-covalent attachment methods can also be used. A number of different chemical modifiers can be used to facilitate attachment formation. Examples of chemical modifiers include N-hydroxy succinimide (NHS) groups, amines, aldehydes, epoxides, carboxyl groups, hydroxyl groups, hydrazides, hydrophobic groups, membranes, maleimides, biotin, streptavidin, thiol groups, nickel chelates, photoreactive groups, boron groups, thioesters, cysteines, disulfide groups, alkyl and acyl halide groups, glutathiones, maltoses, azides, phosphates, and phosphines. These can easily be prepared, for example, using standard methods (Microarray Biochip Technologies, Mark Schena, Editor, March 2000, Biotechniques Books). In some embodiments, attachments are formed between two entities by using an appropriate combination of modifiers (e.g., an electrophilic modifier and a nucleophilic modifier), wherein each entity comprises at least one modifier.

In some embodiments, attachments are formed between two entities by using a chemical modifier present on one of the entities and a naturally occurring moiety, for example, an amine or sulfhydryl, of the other entity. In some embodiments, modifiers that are reactive to amines are used. An advantage of this reaction is that it can be fast and can avoid production of toxic by-products. Examples of such modifiers include NHS-esters, aldehydes, epoxides, acyl halides, and thio-esters. Most proteins, peptides, glycopeptides, etc., have free amine groups, which can react with such modifiers to link them covalently to these modifiers. Nucleic acid probes with internal or terminal amine groups can also be synthesized, and are commercially available (e.g., from IDT or Operon). Thus, biomolecules can be bound (e.g., covalently or non-covalently) to labels, surfaces, or other reagents using similar chemistries.

A number of other multi-functional cross-linking agents can be used to convert the chemical reactivity of one kind of modifier to another. These groups can be bifunctional, tri-functional, tetra-functional, and so on. They can also be homo-functional or hetero-functional. An example of a bi-functional cross-linker is X-Y-Z, where X and Z are two reactive groups, and Y is a connecting linker. Further, if X and Z are the same group, such as NHS-esters, the resulting cross-linker, NHS-Y-NHS, is a homo-bi-functional cross-linker and could connect two entities that each comprise an amine. If X is NHS-ester and Z is a maleimide group, the resulting cross-linker, NHS-Y-maleimide, is a hetero-bi-functional cross-linker and could link an entity comprising an amine with an entity comprising a thio-group. Cross-linkers with a number of different functional groups are widely available. Examples of such functional groups include NHS-esters, thio-esters, alkyl halides, acyl halides (e.g., iodoacetamide), thiols, amines, cysteines, histidines, di-sulfides, maleimide, cis-diols, boronic acid, hydroxamic acid, azides, hydrazines, phosphines, photoreactive groups (e.g., anthraquinone, benzophenone), acrylamide (e.g., acrydite), affinity groups (e.g., biotin, streptavidin, maltose, maltose binding protein, glutathione, glutathione-S-transferase), aldehydes, ketones, carboxylic acids, phosphates, hydrophobic groups (e.g., phenyl, cholesterol), etc.

Other modifier alternatives (such as photo-crosslinking and thermal crosslinking) are known to those skilled in the art. Commercially available technologies include, for example, those from Mosiac Technologies (Waltham, Mass.), EXIQON™ (Vedbaek, Denmark), Schleicher and Schuell (Keene, N.H.), Surmodics™ (St. Paul, Minn.), XENOPORE™ (Hawthorne, N.J.), Pamgene (Netherlands), Eppendorf (Germany), Prolinx (Bothell, Wash.), Spectral Genomics (Houston, Tex.), and COMBIMATRIX™ (Bothell, Wash.).

For single molecule sequencing modalities, the present disclosure can offer the advantage of being able to resequence single molecules. For example, a polymerase can be attached to a nanowell surface, such as at the bottom. A template nucleic acid molecule to be sequenced can be provided in circular form together with a sequencing primer. Resequencing can be achieved by performing a plurality of sequencing cycles such that a sequence read is obtained that is greater than the number of nucleotides in the template nucleic acid molecule. The sequencing read therefore comprises information that redundantly identifies the base in at least one position in the template nucleic acid molecule. In some embodiments, the sequencing read comprises information that redundantly identifies at least 25%, 50%, 75%, 90%, 91%, 92%, 93%, 94%, 95%, 96%, 97%, 98%, 99%, or 100% of the bases in the template nucleic acid molecule. In some embodiments, the sequencing read comprises information that identifies at least 25%, 50%, 75%, 90%, 91%, 92%, 93%, 94%, 95%, 96%, 97%, 98%, 99%, or 100% of the bases in the template nucleic acid molecule with three-fold, four-fold, five-fold, seven-fold, or ten-fold redundancy. By resequencing the same molecule, sequencing errors are expected to fall as the power of the number of sequencing reads. For example, if per base error rates for a single read are $10^{-3}$, then after two reads, this falls to $(10^{-3})^2$, i.e., $10^{-6}$. This is particularly advantageous for single molecule sequencing since the modified nucleotides used for sequencing can lose their labels or blocking groups resulting in, e.g., spurious deletions.

In general, in single molecule sequencing, at least one nucleic acid molecule to be sequenced is contacted with a primer. The primer is modified, e.g., by performing at least one enzyme-catalyzed polymerization or ligation reaction. The at least one reaction leads to emission of light correlated to the identity of at least one base in the nucleic acid. "Leading to" emission of light is understood to mean that the at least one reaction causes at least one condition under which light emission correlated to the identity of at least one base in the nucleic acid occurs; this occurrence may be via interaction with excitatory light, a chemi- or bio-luminescent system, etc. The at least one condition can be, for example, incorporation of a fluorophore into the product of the at least one reaction, or the release of pyrophosphate. Thus, light may be generated with or without external excitation. For example, single molecule sequencing can be performed with reversible terminator base analogs comprising a covalently-linked detectable label, e.g., a fluorescent label, and a blocking group to prevent any secondary extension, wherein the analog is excited and detected after it has been added to the primer, and the label and blocking group are removed after addition to allow another round of extension. Alternatively, a product of an extension step, such as a pyrophosphate, can be detected without external excitation by providing a chemi- or bio-luminescent detection system which emits light in a pyrophosphate-dependent manner. These and other modalities are discussed in more detail below.

The light emitted is correlated to the identity of at least one base in the nucleic acid. In some embodiments, the correlation can be temporal; e.g., the time of emission of the light indicates the identity of the at least one base, such as is the case when different base analogs are provided for use in a polymerization reaction at different times. In some embodiments, the correlation can be spectral; e.g., the spectrum of the emitted light indicates the identity of the at least one base, such as is the case when different base analogs that comprise different fluorophores are provided for use in a polymerization reaction.

In some embodiments, single molecule nucleic acid sequencing comprises multiple sequencing cycles. A sequencing cycle is understood to mean the events that lead to an emission of light correlated to the identity of at least one base that would be repeated in order to identify at least a second base in the nucleic acid after a first base has been identified. Thus, in methods according to the present disclosure that comprise single molecule nucleic acid sequencing, the single molecule nucleic acid sequencing can comprise at least a given number of sequencing cycles that lead to at least the given number of emissions of light correlated collectively to the identity of at least the given number of bases in the nucleic acid, and the method comprises identifying at least the given number of bases in the nucleic acid. In some embodiments, the given number may be, for example, 2, 3, 4, 5, 10, 20, 50, 100, 200, or 500.

Sequencing methods can comprise determining the identity of one or more bases in a nucleic acid. In some embodiments of methods according to the present disclosure, in which performing single molecule nucleic acid sequencing leads to emission of light that is detected with at least one light detector comprising at least a first optical sensor and a second optical sensor, and output signal from the at least two optical sensors is processed, the identity of at least one base in a nucleic acid can be determined by comparing at least one result of the processing with at least one known result corresponding to at least one known type.

For example, a result of the processing can indicate a time at which a reaction occurred; when light emitted is temporally correlated to the identity of at least one base in the nucleic acid, said time can be used to identify at least one base in the nucleic acid.

In another example, a result of the processing can be a determination of which fluorophore was incorporated into the product of a reaction; when light emitted is spectrally correlated to the identity of at least one base in the nucleic acid, said determination can be used to identify at least one base in the nucleic acid.

2.2.2.1 Base Extension Sequencing: Stepwise Extension

In some embodiments, a detection apparatus provided by the present disclosure may be used to detect light generated during base extension sequencing. In some embodiments, base extension sequencing begins by providing a partial duplex sample nucleic acid comprising a single stranded nucleic acid to be sequenced, an end link primer associated with the 3' end of nucleic acid to be sequenced, and a sequencing primer annealed thereto. In some embodiments, polymerase and modified nucleotides may be then applied to the light detection apparatus in a suitable buffer. In some embodiments, the nucleotides may include a covalently-linked detectable label, e.g., a fluorescent label, and a blocking group to prevent any secondary extension. Accordingly, the sequencing pauses after the addition of a single nucleotide to the 3' end of sequencing primer.

In a first step of one embodiment of a base extension sequencing reaction, a nucleotide with a fluorescent blocking group may be added by a DNA polymerase to the 3' end of sequencing primer. In some embodiments, the fluorescent label may act as the blocking group. In other embodiments, they may be separate moieties. A single nucleotide may be incorporated at the 3' end of sequencing primer and is identified by its label by the corresponding light detector. The fluorescent label and blocking group are then removed, e.g., by chemical or enzymatic lysis, to permit additional cycles of base extension. In certain embodiments, the label and blocking groups may be removed simultaneously or sequentially and in any order. By compiling the order of the bases added, the sequence of the sample nucleic acid may be deduced in the 3' to 5' direction, one base at a time.

Generally, there are two ways to recognize the nucleotide added during stepwise extension. In the first case, the four nucleotides may all have the same detectable label, but are added one at a time, in a predetermined order. The identity of the extended nucleotide may be determined by the order that the nucleotide is added in the extension reaction. In the second mode for recognizing the base integrated during extension, four different nucleotides may be added at the same time and each is coupled with a distinct detectable label. In different embodiments, the excitation or emission spectra and/or intensity of the labels may differ. The identity of the nucleotide added in the extension may be determined by the intensity and/or wavelength (i.e., excitation or emission spectra) of the detected label.

2.2.2.2 Sequencing by Synthesis: Multi-Step Extension

In some embodiments, sequencing by synthesis may proceed with multiple uninterrupted extensions, e.g., without the use of blocking groups. In these embodiments, the polymerization reaction may be monitored by detecting the release of the pyrophosphate after nucleoside triphosphate hydrolysis, i.e., the release of the β and γ phosphate complex. This complex may be detected directly, for example, by a fluorescent moiety on the complex, or indirectly, for example, by coupling the pyrophosphate to a chemi- or bio-luminescent detection system, as discussed above.

In some embodiments, the sample nucleic acid may be sequenced essentially continuously by using terminal-phosphate-labeled nucleotides. Exemplary embodiments of terminal-phosphate-labeled nucleotides and methods of their use are described in, e.g., U.S. Pat. No. 7,361,466 and U.S. Patent Publication No. 2007/0141598, published Jun. 21, 2007. Briefly, the nucleotides may be applied to the system provided by the present disclosure and, when hydrolyzed during the polymerization, the labeled pyrophosphate may be detected by a corresponding light detector. In some embodiments, all four nucleotides may comprise distinct labels and be added simultaneously. In some embodiments, the nucleotides may comprise indistinguishable, e.g., identical, labels and be added sequentially in a predetermined order. Sequential, cyclical addition of nucleotides with indistinguishable labels still permits multiple, uninterrupted polymerization steps, e.g., in homopolymer sequences.

2.2.3 Additional Applications

A detection apparatus consistent with the present disclosure may simultaneously detect millions of nucleic acid segments. If each segment is, for example, 1000 bases long, a single device could obtain upwards of billions of base sequences at once. Discussed below are additional applications of the apparatuses and methods provided herein.

2.2.3.1 Whole Genome Sequencing

A detection apparatus consistent with the present disclosure may be used to perform whole or partial genome sequencing of, e.g., a virus, bacterium, fungi, eukaryote, or vertebrate, e.g., a mammal, e.g., a human.

Genomic DNA may be sheared into fragments of at least 20, 50, 100, 200, 300, 500, 800, 1200, 1500 nucleotides, or longer, for sequencing. In some embodiments, the sheared genomic DNA may be from 20 to 50, from 20 to 100, from 20 to 500, from 20 to 1000, from 500 to 1200, or from 500 to 1500 nucleotides long. In some embodiments, the nucleic acids to be sequenced, along with associated end link primers, may be made single stranded, annealed to a sequencing primer, and applied to a system provided by the present disclosure for sequencing as described above.

2.2.3.2 Gene Expression Profiling

In other embodiments, a detection apparatus consistent with the present disclosure may be used to sequence cDNA for gene expression profiling. For example, mRNA levels may be quantified by measuring the relative frequency that a particular sequence is detected on a device. Several million cDNA molecules may be sequenced in parallel on a device provided by the present disclosure. If a cell contains, on average, 350,000 mRNA molecules, a transcript present at even one copy per cell is expected to be sequenced approximately three times in one million sequencing reactions. Accordingly, the devices provided by the present disclosure are suitable for single molecule sequencing with single copy number sensitivity.

cDNA synthesis is well known in the art and typically includes total RNA extraction with optional enrichment of mRNA. cDNA is produced from mRNA by steps including, for example: reverse transcription, for first strand synthesis; RNAse treatment, to remove residual RNA; random hexamer priming of the first strand, and second strand synthesis by DNA polymerase. The resultant cDNA is suitable for sequencing on the devices provided by the present disclosure. Methods of isolating and preparing both DNA and RNA are well known in the art. See, for example, Joseph Sambrook and David Russell, *Molecular Cloning: A Laboratory Manual* Cold Spring Harbor Laboratory Press; 3rd edition (2001).

2.2.3.3 Additional Detection Methods (a) FRET

In some embodiments, a molecule may be detected on a detection apparatus provided by the present disclosure by Förster resonance energy transfer (FRET), sometimes known as fluorescence resonance energy transfer. As is known in the art, FRET occurs when an excited donor molecule non-radiatively transfers energy to an acceptor molecule, which emits the energy, typically as light. FRET can help reduce background light by, e.g., providing greater spectral separation between effective excitation and emission wavelengths for a molecule being detected. FRET is often used to detect close molecular interactions since its efficiency decays as the sixth power of the distance between donor and acceptor molecules. For example, Zhang et al. (*Nature Materials* 4:826-31 (2005)) detected nucleic acid hybridization by FRET. There, a biotinylated nucleic acid target was conjugated to an avidin-coated quantum dot donor, which then excited a Cy5-conjugated DNA probe. In some embodiments, a labeled capture molecule and labeled sample molecule may form a donor/acceptor (or vice versa) pair for detection by FRET.

In some embodiments of nucleic acid sequencing provided by the present disclosure, fluorescently labeled nucleotides may act as acceptor chromophores for a donor chromophore attached to a polymerase or ligase. Accordingly, in these embodiments, the donor chromophore located on the polymerase or ligase may excite an acceptor chromophore on a nucleotide being polymerized on, or ligated to, the sample nucleic acid. Nucleotides not proximate to the polymerase may be not excited due to the rapid falloff in FRET efficiency. In some embodiments the donor molecule may be, e.g., another fluorophore, e.g., a quantum dot. Quantum dots, e.g., semiconductor quantum dots are known in the art and are described in, e.g., International Publication No. WO 03/003015. Means of coupling quantum dots to, e.g., biomolecules are known in the art, as reviewed in, e.g., Medintz et al., *Nature Materials* 4:435-46 (2005) and U.S. Patent Publication Nos. 2006/0068506 and 2008/0087843, published Mar. 30, 2006 and Apr. 17, 2008, respectively. In some embodiments, quantum dots may be conjugated to a DNA polymerase molecule. As already discussed above for conjugating enzymes to linker sites, the skilled artisan will undoubtedly appreciate that when conjugating fluorophores to, e.g., a DNA polymerase or ligase, care must be taken to retain enzyme function by mitigating any effect of conjugating the fluorophore on the primary, secondary, and tertiary structures of the enzyme.

(b) Multi Photon Excitation

In some embodiments, a chromophore may be excited by two or more photons. For example, in some embodiments, excitation of either a donor or acceptor chromophore in FRET may be via two or more photons. Two photon and multiphoton excitation are described further in, e.g., U.S. Pat. Nos. 6,344,653 and 5,034,613.

(c) Time Resolved Detection

In some embodiments, the excitation light source and light detectors of an apparatus provided by the present disclosure may be modulated to have a characteristic phase shift. Using methods known in the art, for example, as disclosed in U.S. Patent Publication No. 2008/0037008, published Feb. 14, 2008, light emitted from a molecule being detected on an apparatus provided by the present disclosure may be measured by a corresponding light detector without interference from an excitation light source.

(d) Other Fluorescent Detection Apparatuses and Methods

In some embodiments, methods of the present disclosure relate to detection of light emitted by at least one object in a biological cell, which can be a living or fixed cell. In some embodiments, the at least one object is chosen from at least one object comprising at least one quantum dot, at least one object comprising at least one fluorescent protein, and at least one object comprising at least one fluorescent small chemical moiety. In some embodiments, the at least one object is fluorescently labeled and comprises at least one oligonucleotide, polynucleotide, oligopeptide, polypeptide, oligosaccharide, polysaccharide, or lipid.

In some embodiments, the at least one object comprises a fixed and limited number of fluorophores, such as at most 20, 10, 5, or 2 fluorophores, which can be chosen from quantum dots, fluorescent proteins, and fluorescent small chemical moieties. In some embodiments, the at least one object comprises a single fluorophore chosen from a quantum dot, a fluorescent protein, and a fluorescent small chemical moiety. Many examples of fluorescent small chemical moieties were discussed above. In some embodiments, fluorescent small chemical moieties may have an emission peak between 300 and 800 nm and/or a quantum yield (fraction of photons emitted per photon of peak absorption wavelength absorbed) of at least 0.1, 0.2, 0.3, 0.4, 0.5, 0.6, 0.7, 0.8, or 0.9.

2.3 Biomolecule Analysis Service

The present disclosure also provides a method of providing biomolecule analysis service using a detection apparatus in accordance with embodiments consistent with the present disclosure. In some embodiments, the method may include the steps of providing a sample including a biomolecule to be analyzed from a service requester to a service provider and the service requester receiving analytical results from the service provider, wherein the results may be produced using an apparatus provided by the present disclosure. In some embodiments, the method may be performed for remunerative consideration, e.g., fee-for-service or contract service agreements. In addition, the sample may be shipped directly between the service requester and the service provider, or mediated by a vendor. In some embodiments, the service provider or vendor may be geographically located in a territory outside of the United States of America, e.g. in another country.

3. EXAMPLES 3.1 Example 1

FIGS. 16A-16D show the computer-simulation results for nanowell 121, 122, 123, and 124 shown in FIG. 3, respectively. In the simulation, a finite-differential-time-domain (FDTD) method was used to compute the electric field distribution of the excitation light propagating along the longitudinal direction of the waveguide and passing by or through the effective excitation zone. The strength of the electric field may represent the intensity of the electromagnetic field of the light in the waveguide. In FIGS. 16A-16D, the strength of the electric field is shown in an arbitrary unit.

In order to more closely simulate the actual situation, in this simulation, a particle having a diameter of 100 nm was assumed to be near the bottom of the nanowell. The refractive index of the particle was set to be 2.5. The refractive index of the core layer was set to be 2.25, the refractive indices of the upper and lower cladding layers were set to be 1.45, the refractive index of the sample solution filling the nanowells was set to be 1.33. The thickness of the core layer was set to be 100 nm. In addition, the diameter of the bottom of the nanowell was set to be 50 nm for all four types of nanowells 121, 122, 123, and 124, and the angle of the side wall of the nanowell with respect to the interface between the core layer and the upper cladding layer was set to be 60 degree. For the simulation for nanowell 121, the bottom of the nanowell was set to be 50 nm away from the interface between the cladding layer and the core layer. For the simulation for nanowell 123, the depth of the nanowell extending in the core layer was set to be 50 nm. That is, the bottom surface of nanowell 123 was set to be located at the center of the core layer. The figures on the left-hand-side of each of FIGS. 16A-16D shows the time-averaged electric field distribution in the waveguide with different nanowells 121, 122, 123, and 124, respectively. The figures on the right-hand-side of each of FIGS. 16A-16D shows the electric field distribution along the vertical direction in the waveguide with different nanowells 121, 122, 123, and 124, respectively.

3.2 Example 2

This example illustrates the simulation results of the transmittances of a TE mode light having a wavelength of 473 nm and TM mode light having a wavelength of 550 nm through a metal pattern as in the structure shown in FIG. 5 as functions of grating period and depth of the metal pattern, respectively.

Figure 17A:
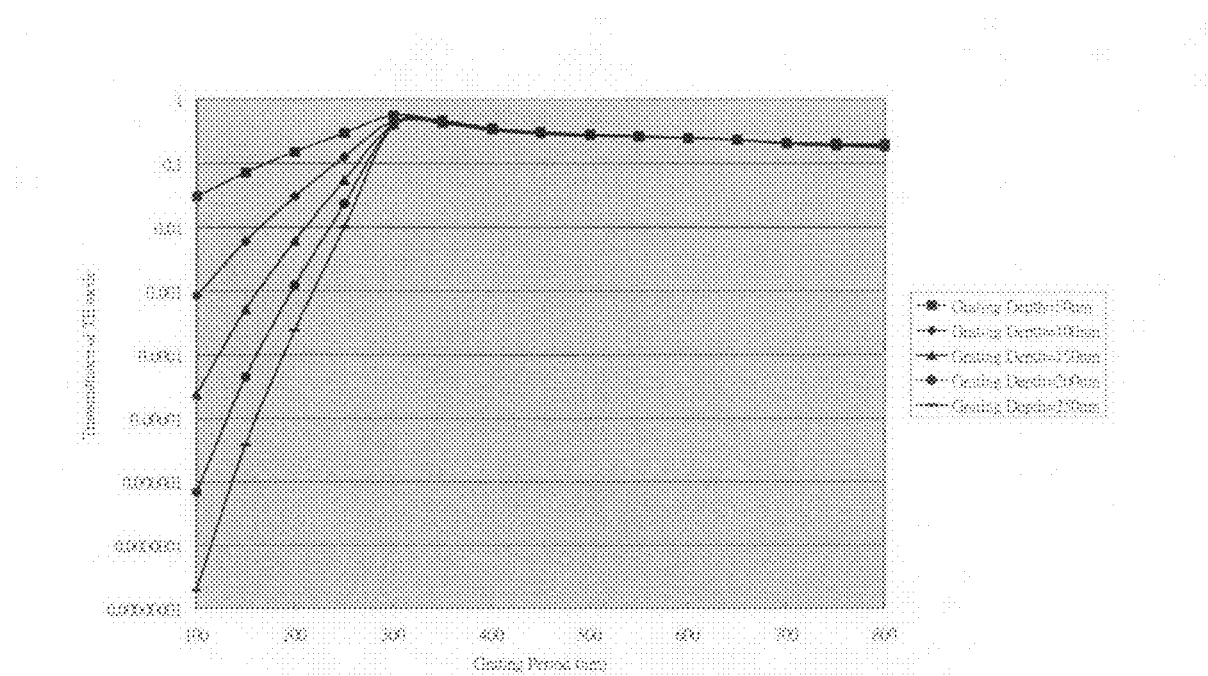
FIGS. 17A and 17B show the dependence of the transmittances of TE and TM lights through a metal grating shown in FIG. 5 on the grating period and depth of the metal grating.
Figure 17B:
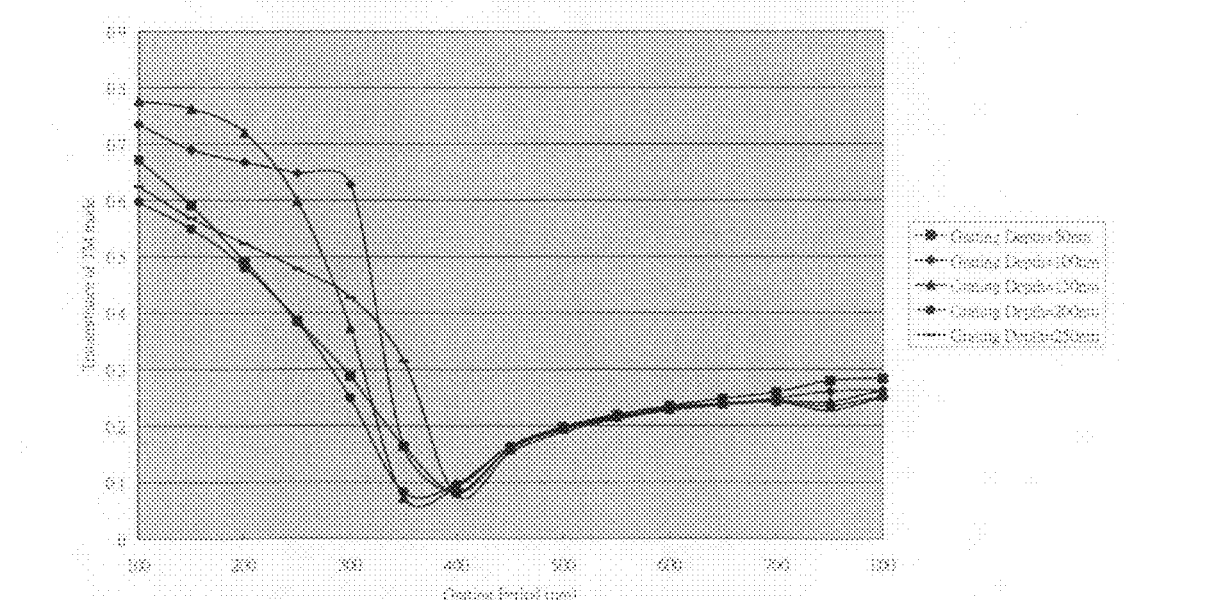

FIG. 17A shows the simulated transmittances of the TE mode light through the metal pattern versus the grating period of the metal pattern. Different curves in FIG. 17A represent results computed at different values of metal pattern depth. FIG. 17B shows the simulated transmittances of the TM mode light through the metal pattern versus the grating period of the metal pattern. Different curves in FIG. 17B represent results computed at different values of metal pattern depth.

Figure 17C:
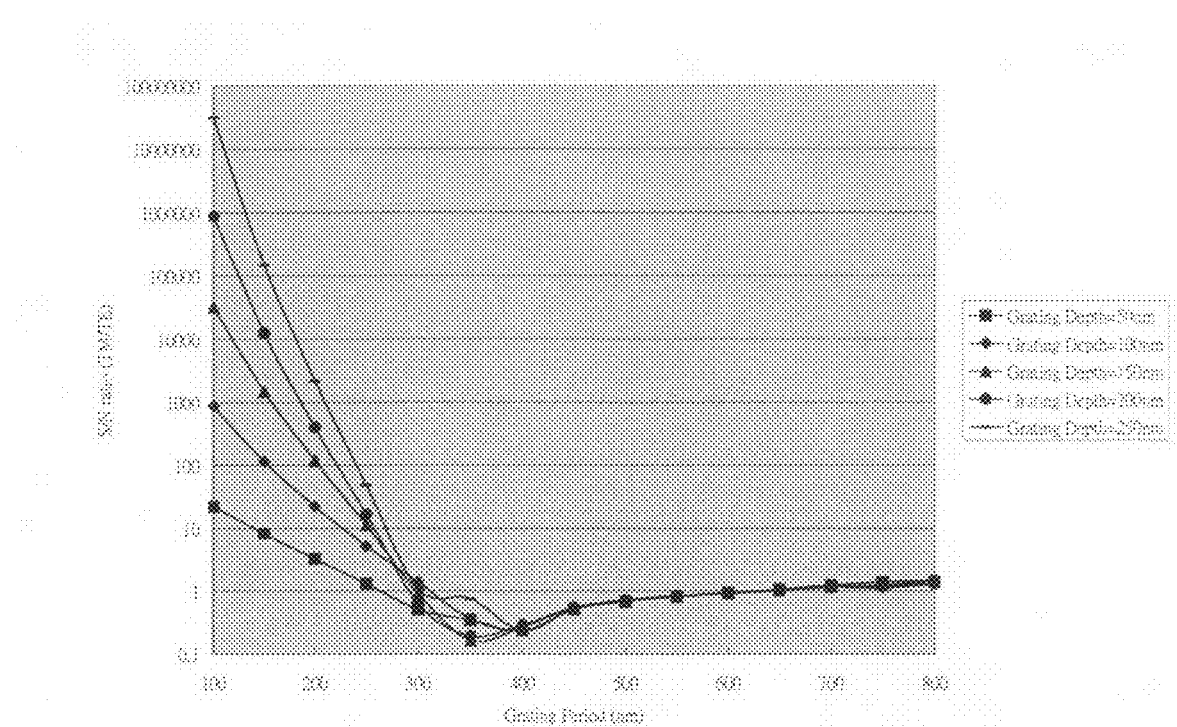
FIG. 17C shows the ratio of the data shown in FIG. 17B to FIG. 17A.

It is seen from FIG. 17B that, when the grating period of the metal pattern is smaller than 300 nm, the transmittance of the TM mode light is higher than about 30%, which is also much higher than the transmittance of the TE mode light. Therefore, it can be expected that a high SNR (i.e., the ratio between the transmittances of the TM mode light and the TE mode light) may be realized with a grating period smaller than 300 nm. FIG. 17C shows the SNR versus the grating period of the metal pattern computed at different values of metal pattern depth. It can be seen that an SNR larger than 10 can be obtained at, for example a grating period of 250 nm and a depth of 150 nm. Furthermore, when the grating period and the depth are 110 nm and 250 nm, respectively, the SNR is larger than $10^7$.

3.3 Example 3

Figure 18A:
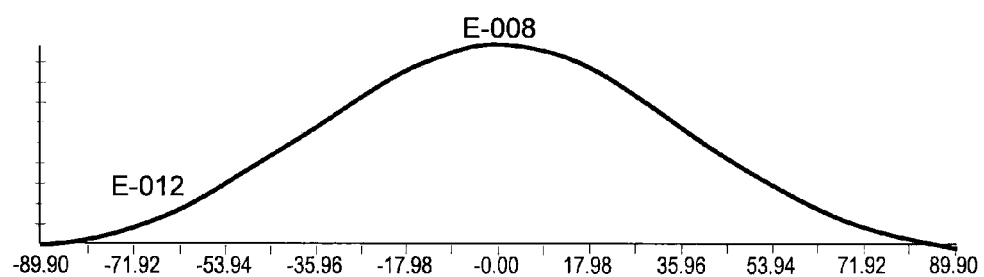
FIGS. 18A and 18B show the dependence of the transmittance of a light through a metal grating shown in FIG. 5 on the incident angle of the light.
Figure 18B:
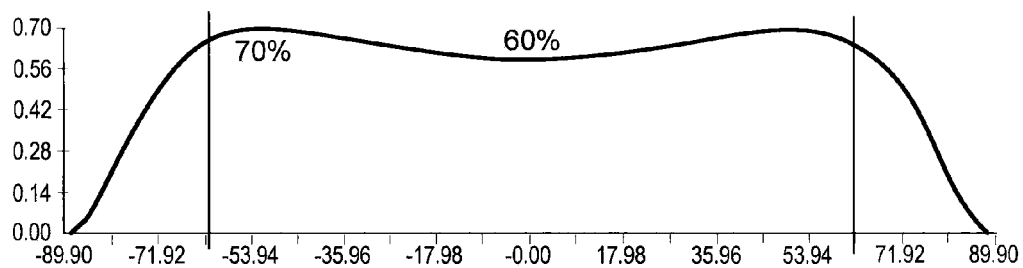

This example illustrates calculated transmittances of a TE mode light and a TM mode light through the metal pattern in the structure shown in FIG. 5. In this example, nanostructured metal pattern 152 is made of aluminum and the lower protection layer 144 surrounding the aluminum pattern is made of silicon oxide. The periodicity and depth of the aluminum pattern are 110 nm and 245 nm, respectively. FIGS. 18A and 18B show the transmittances of the TE mode light and the TM mode light as a function of incident angle, respectively. It is seen from FIGS. 18A and 18B that, the transmittance of the TE mode light decreases from about $10^{-8}$ to about $10^{-12}$ when the absolute value of the incident angle increases from 0 degree to larger than 60 degree, whereas the transmittance of the TM mode light is always higher than 60% within the range of the incident angle from about −60 degree to about 60 degree.

3.4 Example 4

Figure 19:
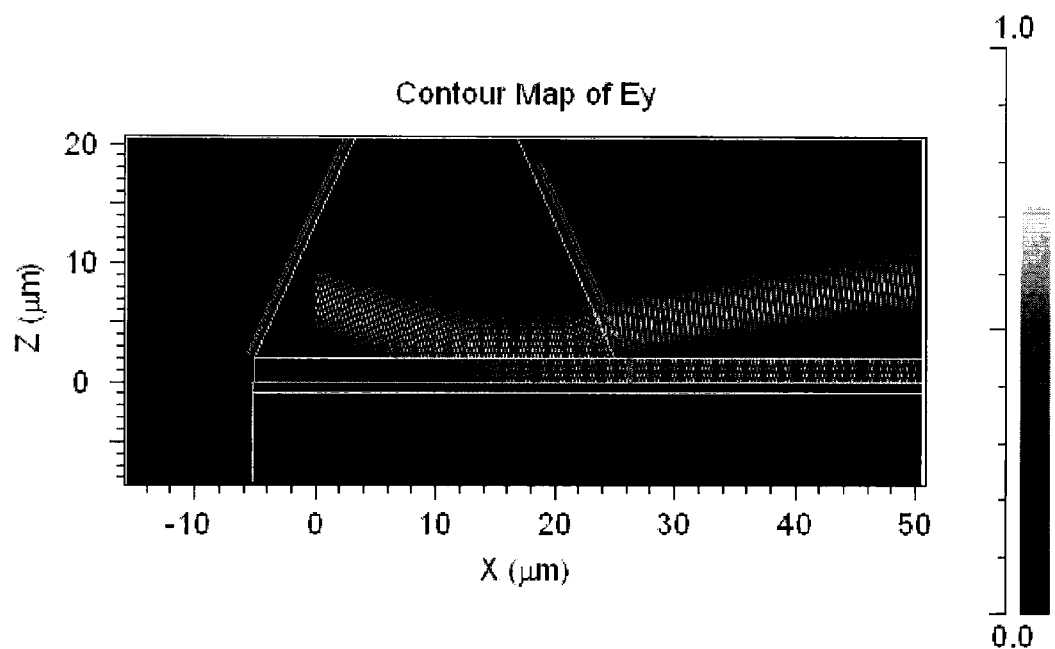
FIG. 19 shows a computer-simulation result for a detection apparatus as shown in FIG. 20.
Figure 20:
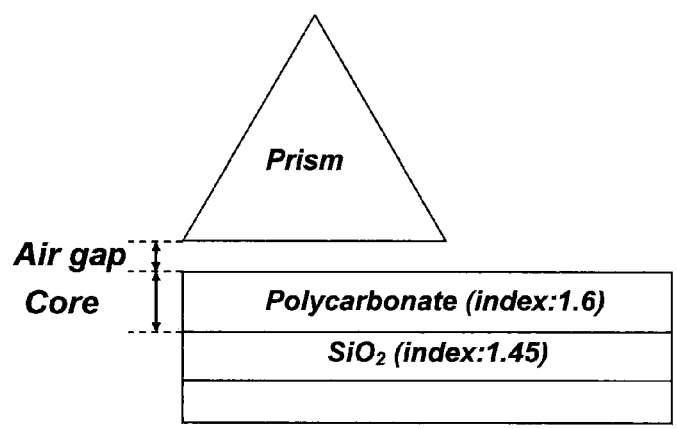
FIG. 20 schematically shows a exemplary detection apparatus using a prism as a coupler.

FIG. 19 shows an FDTD simulation result of a prism coupler shown in FIG. 20. In this simulation, the gap between the prism and the waveguide was set to be 73 nm. Polycarbonate (n=1.6) was used as the material for the core layer, and the thickness of the core layer was set to be 2 µm. The incident light (λ=430 nm) with TM mode was used. Experiments were also conducted to measure the coupling efficiency of the prism coupler, which may be, for example, about 60%. For example, if the light source, such as a He—Ne laser, emits a light with a power of about 2 mW, the power of the light coupled into the waveguide as the excitation light may be about 1.2 mW.

3.5 Example 5

Figure 21:
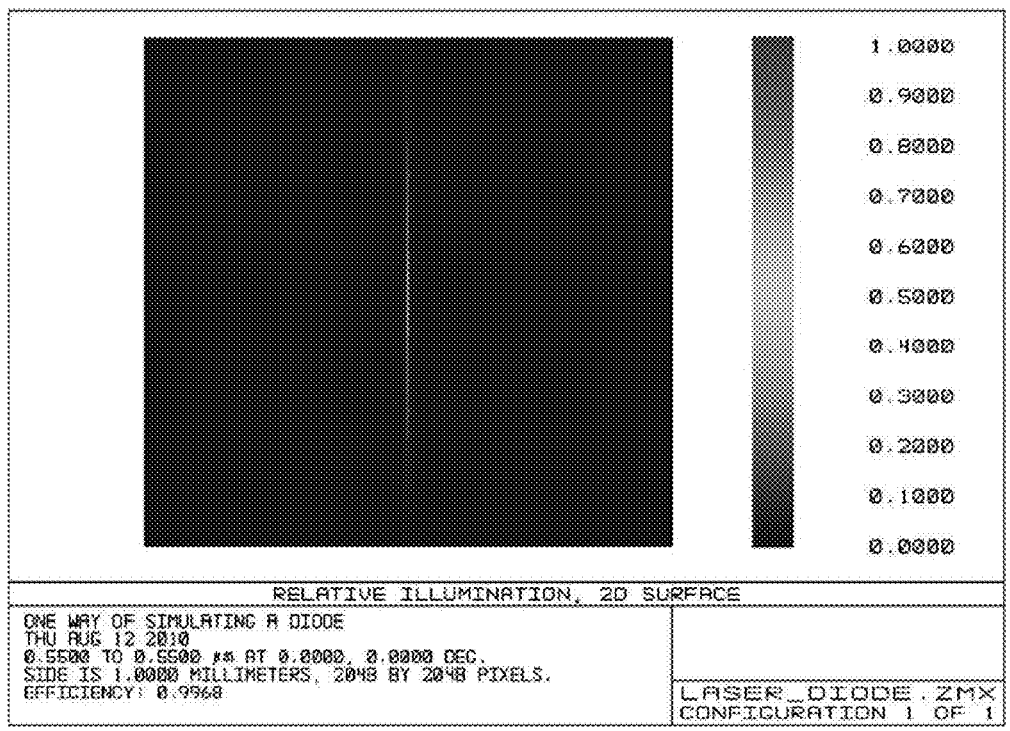
FIG. 21 shows the simulated speckle of the incident light coupled into the waveguide of a detection apparatus as shown in FIG. 7.
Figure 22A:
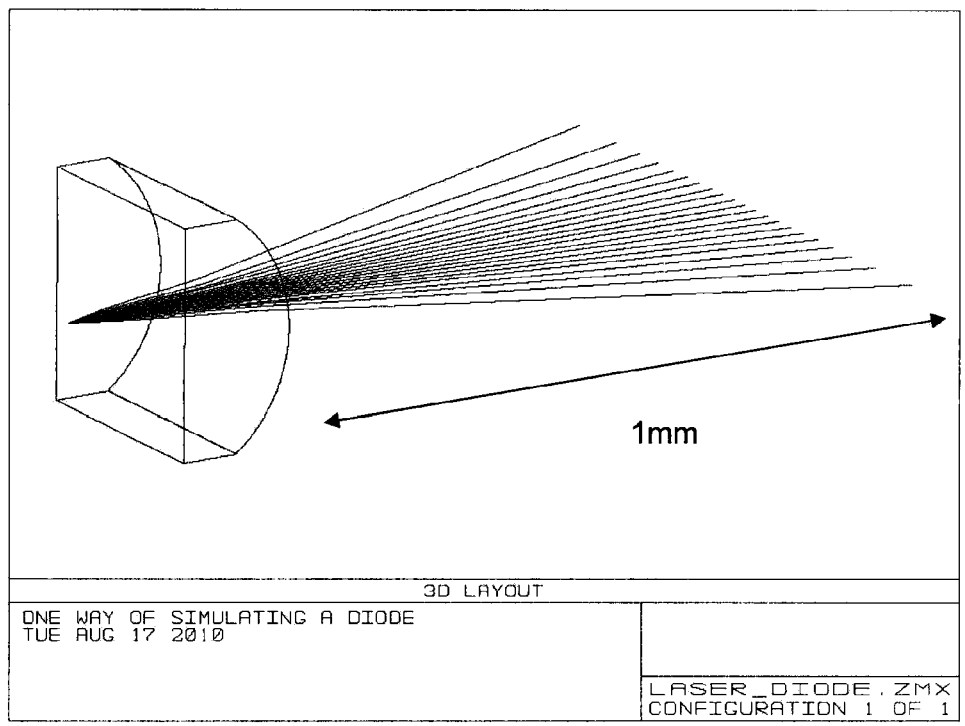
FIGS. 22A and 22B show a lens used in a detection apparatus for the simulation shown in FIG. 20.
Figure 22B:
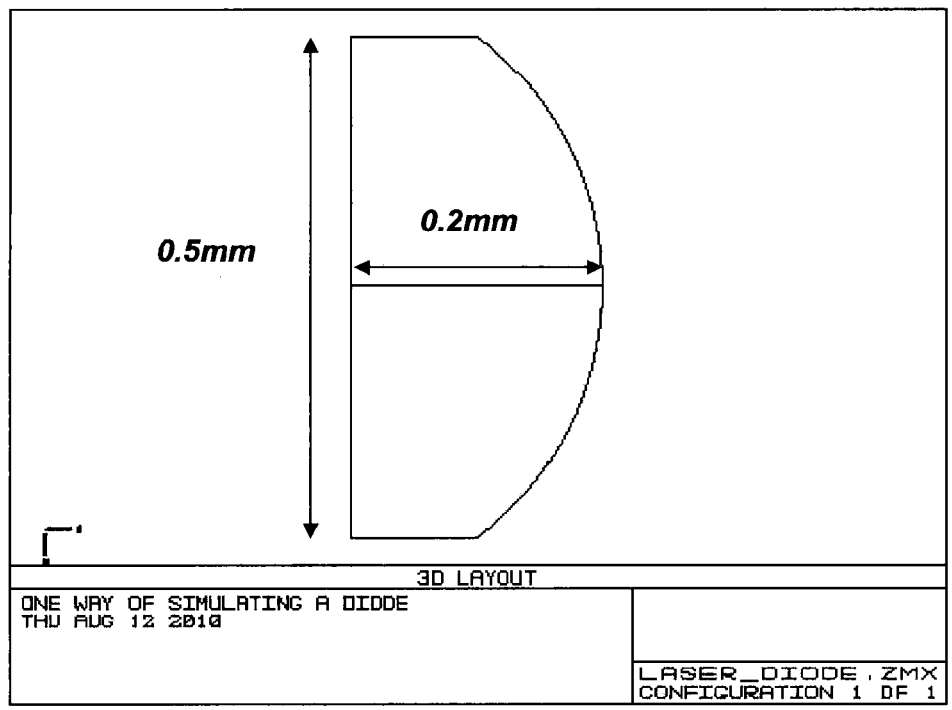

FIG. 21 shows the simulated speckle of the incident light coupled into the waveguide 110 shown in FIG. 7. For this simulation, cylindrical lens made of PMMA with aperture diameter of 0.5 mm and thickness of 0.2 mm was used for laser beam shaping. The projection distance from the lens to waveguide is 1 mm. See FIGS. 22A and 22B. The -thickness of the speckle was about 300 nm and the coupling efficiency was about 70%. For example, if the light source, such as a He—Ne laser, emits a light with a power of about 2 mW, the power of the light coupled into the waveguide as the excitation light may be about 1.4 mW.

3.6 Example 6

Figure 23:
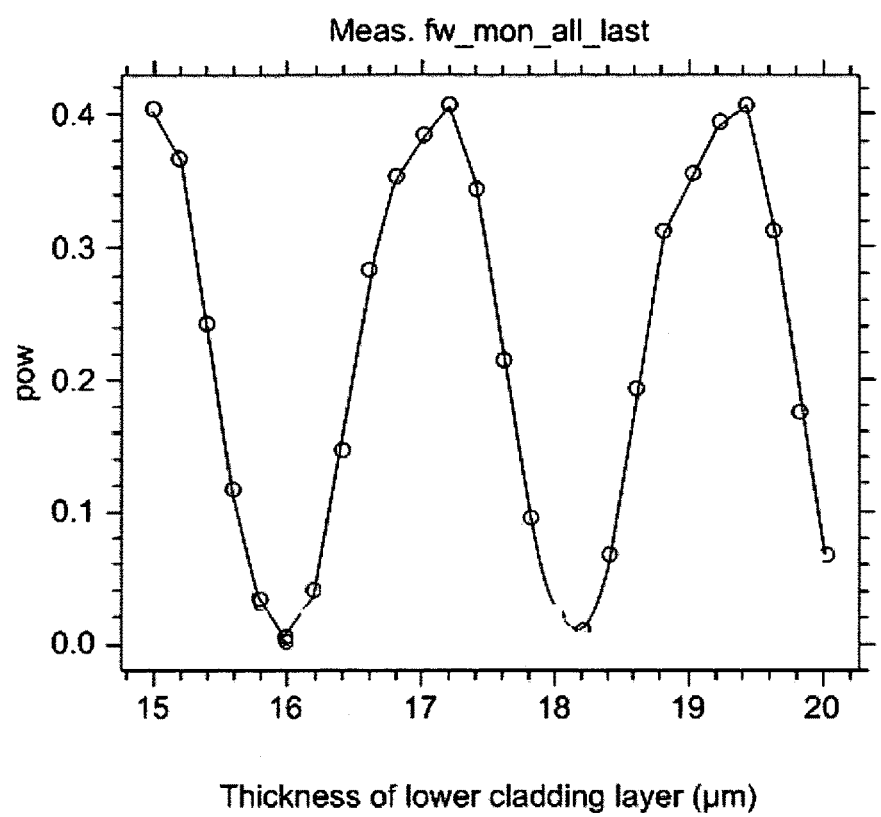
FIG. 23 shows measured power of lights coupled into the waveguide of a detection apparatus as shown in FIG. 9.

FIG. 23 shows, as an example, the measured dependence of the power of the light coupled into the core layer 112 on the thickness of the lower cladding layer 116 for the waveguide shown in FIG. 9. In this measurement, the grating period was about 410 nm and the thickness of the core layer was about 100 nm. The wavelength of the incident light was about 633 nm. In FIG. 23, the power of the light coupled into the core layer is normalized with respect to the incident power.

3.7 Example 7

Figure 24:
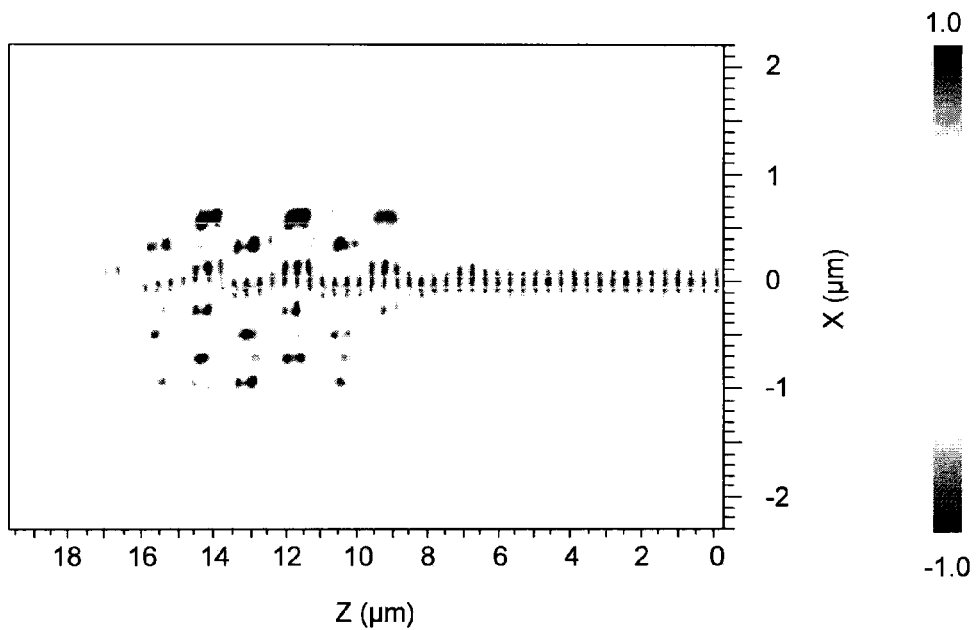
FIG. 24 shows a computer-simulation result for a detection apparatus as shown in FIG. 8.
Figure 25:
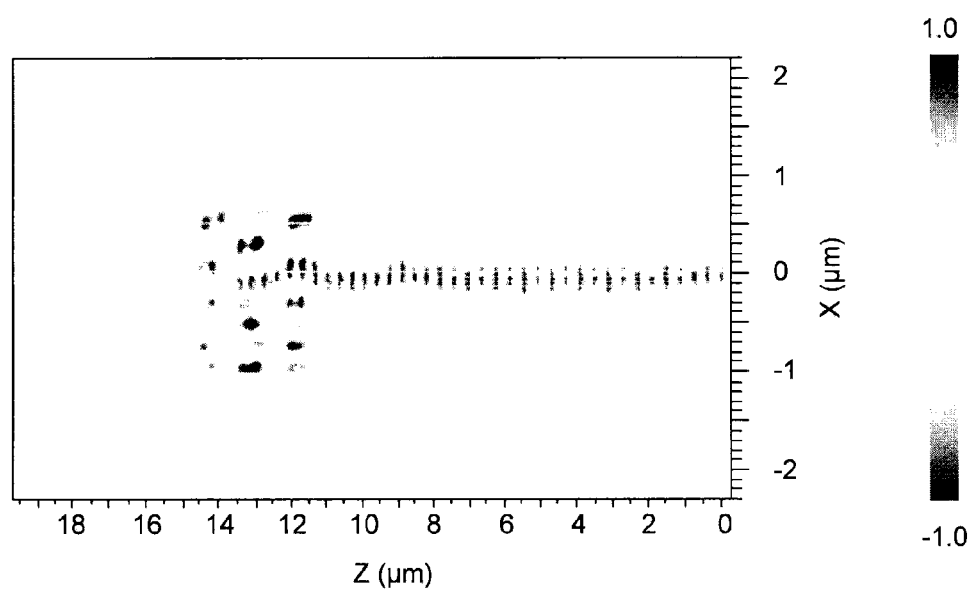
FIG. 25 shows a computer-simulation result for a detection apparatus as shown in FIG. 9.

An FDTD simulation was performed on the grating couplers shown in FIGS. 8 and 9, respectively. In the simulation, the periodicity of the first grating in FIGS. 8 and 9 was set to be 410 nm and the periodicity of the second grating in FIG. 9 was set to be 300 nm. The depths of both gratings were set to be 55 nm. The incident light was set to have a wavelength of 473 nm and a beam radius of 5 µm; the refractive indices of the core and cladding layers were set to be 2.196 and 1.445, respectively. FIGS. 24 and 25 show the simulated instantaneous electric field distribution in the structures shown in FIGS. 8 and 9, respectively. The calculated coupling efficiencies for the structures shown in FIGS. 8 and 9 were 20% and 25%, respectively, which confirms the increasing of coupling efficiencies by adding the second grating 404.

3.8 Example 8

Figure 11:
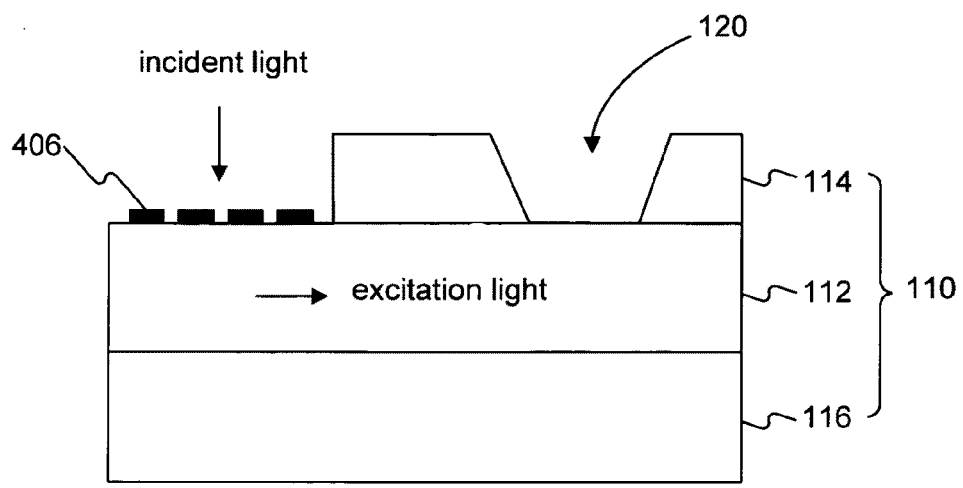
FIG. 11 is a schematic view showing a detection apparatus according to one embodiment of the present disclosure.

A calculation was performed on such a structure shown in FIG. 11. For the calculation, the effective refractive index of the grating 406 was set to be 2.2, the refractive indices of the core layer 112 and the cladding layers 114 and 116 were set to be 1.6 and 1.45, respectively, and the periodicity and depth of the grating were set to be 321 nm and 120 nm, respectively. Under such conditions, for an incident light with a wavelength of 473 nm and normally incident onto the grating 406, the calculated coupling efficiency was 29%.

3.9 Example 9

Table 1 shows the calculation results of the power density of the light emitted from an absorbing-emitting light coupler using phthalocyanine, 4-(dicyanomethylene)-2-methyl-6-(p-dimethylaminostyryl)-4H-pyran (DCM) doped polyvinylphyrodione (PVP) as the photoluminescence material under different conditions. It is seen from Table 1 that, for a same incident light, the power density of the light coupled into the waveguide may be as high as 37.67 W/cm².

TABLE 1

| Photoluminescence material | DCM doped PVP | DCM doped PVP | DCM doped PVP |
|---|---|---|---|
| $d_1$ (cm) | 0.0002 | 0.0002 | 0.0002 |
| $d_2$ (cm) | 2.0 | 2.0 | 2.0 |
| L (cm) | 3.0 | 3.0 | 3.0 |
| Photoluminescence material concentration (M) | 0.04 | 0.04 | 0.04 |
| $\lambda_1$ (nm) | 465 | 465 | 465 |
| $\lambda_2$ (nm) | 630 | 630 | 630 |
| Stokes shift ($\lambda_1 - \lambda_2$, nm) | 165 | 165 | 165 |
| $P_0(\lambda_1)$ (W) | 1.0 | 1.0 | 1.0 |
| Power density of incident light at $\lambda_1$ (W/cm²) | 1.0 | 1.0 | 1.0 |
| $\phi_{FL}$ | 0.6 | 0.6 | 0.6 |
| $R_1$ | 0.90 | 0.90 | 0.90 |
| $\eta_c$ | 0.0850 | 0.0850 | 0.1850 |
| $P(\lambda_2)/P_0(\lambda_1)$ | 0.0060 | 0.0103 | 0.0226 |
| Power density of excitation light at $\lambda_2$ (W/cm²) | 9.92 | 17.17 | 37.67 |

3.10 Example 10

A DNA molecule is sequenced using the detection apparatus disclosed herein. The detection apparatus of this example comprises a light source, a light coupler, a planar waveguide having a nanowell array formed in the upper cladding layer of the waveguide, and a detector array formed beneath the waveguide.

In this example, the light source is a He—Ne laser emitting a light having a wavelength of about 633 nm. The power of the He—Ne laser is about 2 mW. The light coupler is a side coupler consisting of a cylindrical lens made of PMMA. The cylindrical lens has an aperture diameter of about 0.5 mm and a thickness of about 0.2 mm, and is arranged at a distance of about 1 mm from the side of the waveguide. The detector array consists of 1000 light detectors, each of which is a silicon photodiode.

The planar waveguide comprises a core layer having a thickness of about 100 nm, an upper cladding layer, and a lower cladding layer. The core layer is made of silicon nitride having a refractive index of about 2.05. The upper and lower cladding layers are made of silicon oxide having a refractive index of about 1.46. The nanowell array formed in the upper cladding layer contains 1000 nanowells. For each of the nanowells, there is a light detector used to detect the light emitted by the molecule trapped in the nanowell.

Each nanowell has a funnel shape with a circular horizontal cross-section. The nanowells extend through the full thickness of the upper cladding layer so as to expose the core layer. The diameter of the bottom of the nanowell is about 50 nm. The angle between the sidewall of the nanowell and the vertical direction is about 30 degrees. The effective excitation zone formed in each nanowell is about 1 atto liter (al).

Nucleic acid polymerases are chemically attached to the bottom surfaces of nanowells with an average density of about 1 active, accessible polymerases per nanowell effective excitation zone.

A solution of circular, single-stranded DNA molecules with an average length of 200 nt at a concentration of 0.1 molecules per atto liter in a suitable sequencing reaction buffer is applied to the detection apparatus. The circular DNA molecules contain a known insert sequence of approximately 20 nt 3' to an unknown sample sequence. A sequencing primer complementary to the known insert sequence and fluorescently labeled dNTP analogs with blocking groups suitable for reversible terminator sequencing by synthesis are provided. In a plurality of nanowells, a ternary complex of a polymerase, DNA molecule, and sequencing primer is formed and the polymerase adds one fluorescently labeled dNTP analog to the 3' end of the sequencing primer.

Light emitted from the He—Ne laser is partially coupled into the waveguide by the side coupler. Some of the light coupled into the waveguide propagates in the core layer, acting as the excitation light. In the plurality of nanowells, a fluorescently labeled dNTP analog is excited by the excitation light entering the effective excitation zones formed near the bottom of the nanowells and emits fluorescent light. This fluorescent light is detected by the detectors, which in turn generate output signals to be processed to identify the base comprised by the nucleotide analog added to the sequencing primer.

In the plurality of nanowells, the fluorophore and the blocking group are chemically removed. The polymerase then adds another fluorescently labeled dNTP analog, which is detected as above and then removed. This cycle is repeated a sufficient number of times to acquire a sequencing read at least twice the length of the DNA molecule (i.e., the DNA molecule is sequenced and resequenced).

What is claimed is:

1. A single molecule detection apparatus, comprising:
   a) a waveguide comprising:
      a core layer; and
      a first cladding layer made of a dielectric material, wherein
      at least one nanowell is formed in at least the first cladding layer, and
      an upper opening of the at least one nanowell is larger than a bottom of the at least one nanowell;
   b) a first opaque protection layer arranged over the first cladding layer without extending into the at least one nanowell;
   c) a second opaque protection layer arranged below the waveguide, the second opaque protection layer having a nanostructured metal pattern; and
   d) at least one light detector.

2. The detection apparatus of claim 1, further comprising a light source.

3. The detection apparatus of claim 2, further comprising a light coupler.

4. The detection apparatus of claim 1, wherein an effective excitation zone is formed near the bottom of the at least one nanowell by a light field induced from a light wave propagating along the core layer.

5. The detection apparatus of claim 1, wherein the at least one nanowell and the detector are arranged at opposite sides of the waveguide.

6. The detection apparatus of claim 1, wherein the light detector generates a signal based on a detected light.

7. The detection apparatus of claim 1, wherein the waveguide is a planar waveguide further comprising a second cladding layer, the first cladding layer and the second cladding layer being arranged at opposite sides of the core layer.

8. The detection apparatus of claim 1, wherein the at least one nanowell extends through partial thickness of the first cladding layer.

9. The detection apparatus of claim 1, wherein the at least one nanowell extends through full thickness of the first cladding layer.

10. The detection apparatus of claim 1, wherein the at least one nanowell extends through full thickness of the first cladding layer and partial thickness of the core layer.

11. The detection apparatus of claim 7, wherein the at least one nanowell extends through full thickness of the first cladding layer and full thickness of the core layer.

12. The detection apparatus of claim 1, wherein the light detector comprises a set of optical sensors.

13. The detection apparatus of claim 1, further comprising a plurality of nanowells forming a nanowell array.

14. The detection apparatus of claim 13, further comprising a plurality of light detectors forming a detector array, each light detector in the detector array corresponding to at least one nanowell in the nanowell array.

15. The detection apparatus of claim 1, wherein the core layer has a higher refractive index than the first cladding layer.

16. The detection apparatus of claim 7, wherein the core layer has a higher refractive index than the first and second cladding layers.

17. The detection apparatus of claim 1, wherein the core layer is made from a material chosen from at least one of $Si_xTi_{1-x}O_2$, $TiO_2$, $Ta_2O_5$, $Nb_2O_5$, $HfO_2$, $Al_2O_3$, $ZrO_2$, $ZnS$, $SiN_x$, $AlN_x$, $TiN_x$, PC, PMMA, or Su8.

18. The detection apparatus of claim 1, wherein the first cladding layer is made from a material chosen from at least one of $SiO_2$, $MgF_2$, $CaF_2$, $Al_2O_3$, PMMA, Su8, or polycarbonate.

19. The detection apparatus of claim 7, wherein the first cladding layer and the second cladding layer are made from a material chosen from at least one of $SiO_2$, $MgF_2$, $CaF_2$, $Al_2O_3$, PMMA, Su8, or polycarbonate.

20. The detection apparatus of claim 1, wherein the first opaque protection layer is made from a material chosen from at least one of Al, Ti, Ni, Cr, Au, Ag, Cu, Pt, Pd, or an alloy of any two or more thereof.

21. The detection apparatus of claim 1, wherein the second opaque protection layer is made from a material chosen from Al, Ti, Ni, Cr, Au, Ag, Cu, Pt, Pd, or an alloy of any two or more thereof.

22. The detection apparatus of claim 1, wherein an optical filter is arranged between the waveguide and the light detector.

23. The detection apparatus of claim 7, wherein an optical filter is arranged between the second cladding layer and the light detector.

24. The detection apparatus of claim 1, wherein an optical filter is arranged between the second opaque protection layer and the light detector.

25. The detection apparatus of claim 7, wherein the second cladding layer also serves as an optical filter.

26. The detection apparatus of claim 1, further comprising a cover over the at least one nanowell.

27. The detection apparatus of claim 1, wherein at least a first surface of the at least one nanowell has different surface property than at least a second surface of the at least one nanowell.

28. The detection apparatus of claim 1, wherein a sidewall surface of the at least one nanowell is hydrophilic, the sidewall surface comprising a material chosen from silicon, silica, metal, or metal oxide.

29. The detection apparatus of claim 1, wherein a bottom surface of the at least one nanowell is hydrophobic.

30. The detection apparatus of claim 29,
wherein the bottom surface of the at least one nanowell is formed from a silicate or a metal with a hydrophilic property modified, by $R1_x\text{-}Si(O\text{—}R2)_{4-x}$ or a polymer with a functional group, to hydrophobic, and
wherein
R1 is a hydrophobic group chosen from alkyl chain $—(CH_2)_n—CH_3$ and R2 is $C_nH_{2n+1}$, and
the functional group is chosen from —COOH, $—PO_3H_2$, —SH, or $NH_2$.

31. The detection apparatus of claim 29,
wherein the bottom surface of the at least one nanowell is formed from a metal oxide with a hydrophilic property modified, by $R1_x\text{-}Si(O\text{—}R2)_{4-x}$, or a polymer with a functional group, to hydrophobic, and
wherein
R1 is a hydrophobic group chosen from alkyl chain $—(CH_2)_n—CH3$ and R2 is $C_nH_{2n+1}$, and
the functional group is chosen from —COOH, $—PO_3H_2$, —SH, or $NH_2$.

32. The detection apparatus of claim 1, wherein a bottom of the at least one nanowell has a different surface property from that of a sidewall surface of the at least one nanowell.

33. The detection apparatus of claim 27, wherein the surface property comprises hydrophobicity, functional group, functional group density, material density, or conductivity.

34. The detection apparatus of claim 32, wherein the surface property comprises hydrophobicity, functional group, functional group density, material density, or conductivity.

35. The detection apparatus of claim 3, wherein the light coupler is a grating coupler located over the core layer, in the core layer, or beneath the core layer.

36. The detection apparatus of claim 3, wherein the light coupler is a prism coupler.

37. The detection apparatus of claim 3, wherein the light coupler is a side coupler.

38. The detection apparatus of claim 3, wherein the light coupler is an absorbing-emitting coupler, which absorbs an incident light emitted from the light source and emits an excitation light.

39. The detection apparatus of claim 38, wherein the absorbing-emitting coupler comprises a photoluminescent material having a Stokes shift greater than or equal to 30 nm.

40. The detection apparatus of claim 39, wherein the photoluminescent material is doped in a polymer.

41. The detection apparatus of claim 39, wherein the photoluminescent material comprises a photoluminescent dye, the photoluminescent dye comprising anthracene, coumarin, pyrene, stilbene, porphyrin, perylene, Alq3, eosin, Bodipy dye, fluorescein, rhodamine, polymethine dye, DCM, or its derivative.

42. The detection apparatus of claim 39, wherein the photoluminescent material comprises a photoluminescent polymer, the photoluminescent polymer comprising PPV or its derivative.

43. The detection apparatus of claim 39, wherein the photoluminescent material comprises an inorganic compound, the inorganic compound comprising quantum dot, alumina oxide, or zinc oxide.

44. The detection apparatus of claim 3, wherein the light coupler is a co-directional coupler.

45. The detection apparatus of claim 2, wherein the light source is a laser, a laser diode, an LED, an OLED, a QLED, a fiber light source, or an arc discharge fluorescent lamp.

46. The detection apparatus of claim 1, wherein the first cladding layer has a refractive index approximately equal to that of a sample solution.

47. The detection apparatus of claim 1, wherein the first cladding layer has a refractive index larger than that of a sample solution.

48. The detection apparatus of claim 1, wherein a size of a bottom of the at least one nanowell is smaller than a wavelength of an excitation light in the core layer, smaller than one-half of the wavelength, smaller than one-quarter of the wavelength, or smaller than one-eighth of the wavelength.

49. The detection apparatus of claim 1, wherein the light detector is an optical sensor chosen from a CCD, a CMOS optical sensor, a photoconductive type optical sensor, a photovoltaic type optical sensor, an APD, a p-n photodiode, a p-i-n photodiode, or a multi-junction photodiode.

50. The detection apparatus of claim 1, wherein the light detector is a set of optical sensors chosen from CCDs, CMOS optical sensors, photoconductive type optical sensors, photovoltaic type optical sensors, APDs, p-n photodiodes, p-i-n photodiodes, or multi-junction photodiodes.

51. The detection apparatus of claim 50, wherein the optical sensors in one set have different sensitive wavelength bands.

52. A method of detecting a single molecule, comprising:
emitting, by a light source, an incident light;
coupling, by a coupler, the incident light into a waveguide, forming an excitation light in the waveguide;

forming, by the excitation light and at least one nanowell formed in at least a cladding layer of the waveguide, an effective excitation zone, the cladding layer being formed of a dielectric material, a first opaque protection layer being arranged over the cladding layer without extending into the at least one nanowell, a second opaque protection layer arranged below the waveguide, the second opaque protection layer having a nanostructured metal pattern, and an upper opening of the at least one nanowell being larger than a bottom of the at least one nanowell;

locating a single molecule object in the effective excitation zone; and exciting, by the excitation light, the single molecule object in the effective excitation zone, to cause the single molecule object to emit a light to be detected by a light detector.

* * * * *